United States Patent
Rantanen et al.

(10) Patent No.: US 11,666,714 B2
(45) Date of Patent: Jun. 6, 2023

(54) INHALER WITH ACOUSTIC FLOW MONITORING

(71) Applicant: Københavns Universitet, Copenhagen K (DK)

(72) Inventors: Jukka Rantanen, Slangerup (DK); Claus Cornett, Valby (DK); Johan Peter Bøtker, Søborg (DK); Henrik Jensen, Roskilde (DK); Adam Bohr, Frederiksberg (DK)

(73) Assignee: KØBENHAVNS UNIVERSITET, Copenhagen (DK)

( * ) Notice: Subject to any disclaimer, the term of this patent is extended or adjusted under 35 U.S.C. 154(b) by 718 days.

(21) Appl. No.: 16/624,826

(22) PCT Filed: Jun. 22, 2018

(86) PCT No.: PCT/DK2018/050164
§ 371 (c)(1),
(2) Date: Dec. 19, 2019

(87) PCT Pub. No.: WO2018/233794
PCT Pub. Date: Dec. 27, 2018

(65) Prior Publication Data
US 2020/0114096 A1    Apr. 16, 2020

(30) Foreign Application Priority Data

Jun. 23, 2017 (DK) .......................... PA 2017 70492

(51) Int. Cl.
*A61M 15/00*    (2006.01)

(52) U.S. Cl.
CPC .... *A61M 15/0086* (2013.01); *A61M 15/0021* (2014.02); *A61M 2205/3569* (2013.01);
(Continued)

(58) Field of Classification Search
CPC .. A61M 15/00–085; A61M 16/00–022; A61M 2016/0015–0135;
(Continued)

(56) References Cited

U.S. PATENT DOCUMENTS

| 6,240,917 B1 | 6/2001 | Andrade |
| 6,578,571 B1 * | 6/2003 | Watt ................. A61M 15/0016 128/200.14 |

(Continued)

FOREIGN PATENT DOCUMENTS

| EP | 0013534 A1 | 7/1980 | |
| GB | 2299512 A * | 10/1996 | ........ A61M 15/0086 |

(Continued)

OTHER PUBLICATIONS

International Search Report for PCT/DK2018/050164 dated Sep. 17, 2018.
DK Search Report for PA 2017 70492 dated Oct. 24, 2017.

*Primary Examiner* — Valerie L Woodward
*Assistant Examiner* — Paige Kathleen Bugg
(74) *Attorney, Agent, or Firm* — Knobbe, Martens, Olson & Bear, LLP

(57) ABSTRACT

An inhaler or add-on device for an inhaler for dispensing a medicament to be inhaled. The inhaler or add-on device has a housing (H) with an air inlet (A_I), and an air outlet (A_O) for outputting air to be inhaled by a user. The housing (H) defines a flow path (FP) between the air inlet (A_I) and air outlet (A_O), and a passive acoustic element (PAE) is arranged in this flow path (FP) inside the housing (H). The passive acoustic element (PAE) has a structure having one or more structured gaps arranged to be passed by an air flow and it is dimensioned such that air flow passing it will generate sound (S) with pre-determined characteristics depending on the air flow speed. This allows acoustic (Continued)

monitoring of air flow passing the first passive acoustic element (PAE) external to the housing (H) by capturing and processing sound generated.

31 Claims, 27 Drawing Sheets

(52) U.S. Cl.
CPC ............... *A61M 2205/3584* (2013.01); *A61M 2205/3592* (2013.01); *A61M 2205/43* (2013.01); *A61M 2205/581* (2013.01)

(58) Field of Classification Search
CPC .. A61M 2205/3569; A61M 2205/3584; A61M 2205/3592; A61M 2205/43; A61M 2205/581
USPC .......................................................... 600/538
See application file for complete search history.

(56) References Cited

U.S. PATENT DOCUMENTS

| | | | |
|---|---|---|---|
| 6,718,969 B1 * | 4/2004 | Rubin ............... | A61M 16/0833 482/13 |
| 6,990,976 B2 * | 1/2006 | Miyamoto ........ | A61M 15/0028 128/200.23 |
| 9,138,167 B1 | 9/2015 | Leydon | |
| 2006/0107755 A1 | 5/2006 | Kuo | |
| 2007/0272235 A1 | 11/2007 | Miyamoto | |
| 2012/0318261 A1 * | 12/2012 | Newhouse ........ | A61M 15/0016 128/200.23 |
| 2014/0007867 A1 * | 1/2014 | Bruin .................... | A61M 11/04 128/200.23 |
| 2014/0251330 A1 | 9/2014 | Collins et al. | |
| 2014/0305440 A1 | 10/2014 | Root | |
| 2016/0166766 A1 | 6/2016 | Schuster et al. | |
| 2017/0216538 A1 * | 8/2017 | Kinsey .............. | A61M 15/0045 |
| 2017/0333645 A1 * | 11/2017 | Alizoti ................ | A61B 5/4833 |
| 2018/0064402 A1 * | 3/2018 | Leydon ............. | A61M 15/0021 |
| 2019/0351159 A1 * | 11/2019 | Lisberg ............. | A61M 15/0021 |
| 2021/0225477 A1 * | 7/2021 | Kay ....................... | A61B 5/087 |

FOREIGN PATENT DOCUMENTS

| | | | | |
|---|---|---|---|---|
| GB | 2299512 A | | 10/1996 | |
| GB | 2372704 A | * | 9/2002 | ............. A61B 5/087 |
| GB | 2372704 A | | 9/2002 | |
| JP | 59-126300 U | | 8/1984 | |
| WO | WO 2016/116629 A1 | | 7/2016 | |

* cited by examiner

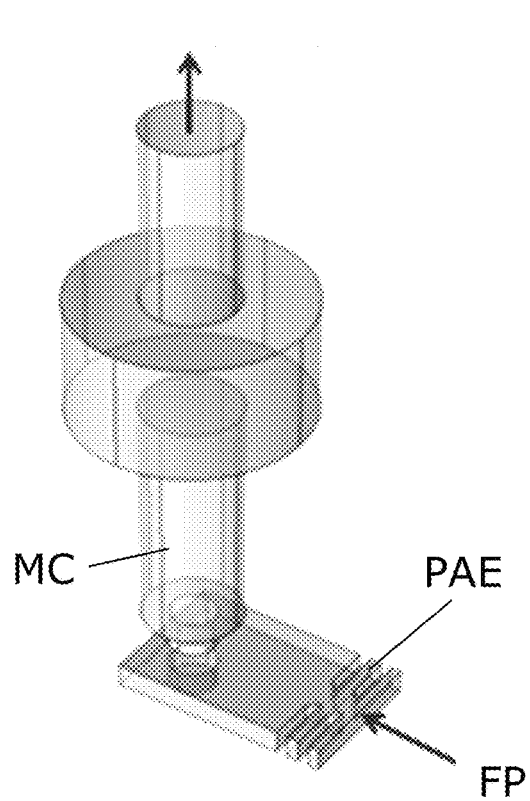
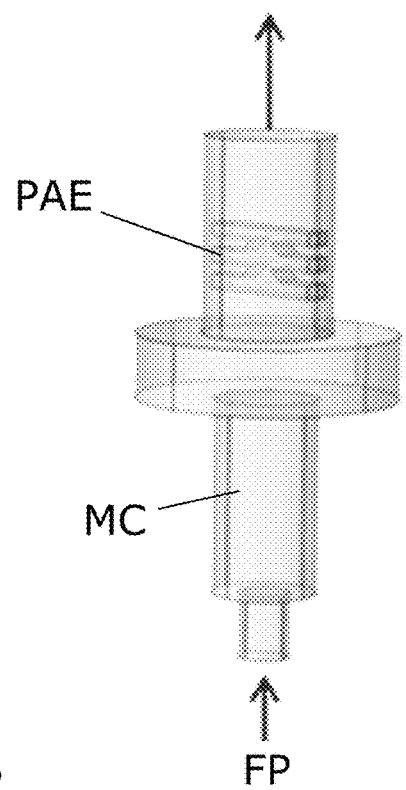
FIG. 3          FIG. 4
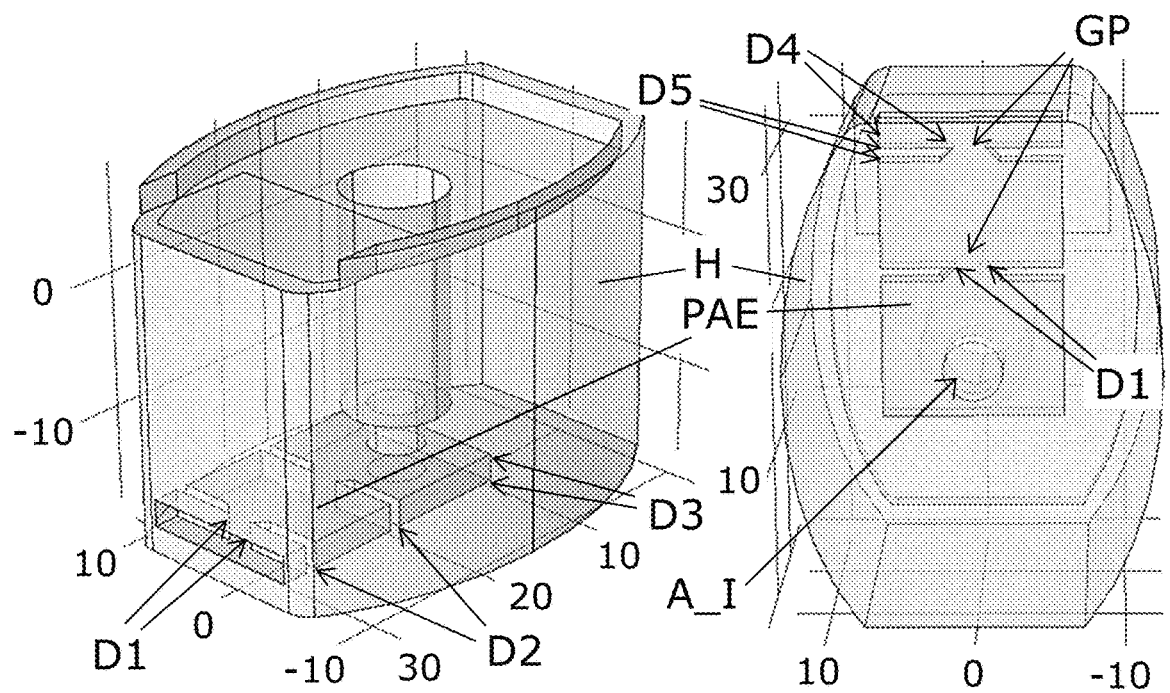
FIG. 5a          FIG. 5b

INHALER WITH ACOUSTIC FLOW MONITORING

CROSS REFERENCE TO RELATED APPLICATIONS

This application is a U.S. National Phase Application of PCT International Application Number PCT/DK2018/050164, filed on Jun. 22, 2018, designating the United States of America and published in the English language, which is an International Application of and claims the benefit of priority to Danish Patent Application No. PA 2017 70492, filed on Jun. 23, 2017. The disclosures of the above-referenced applications are hereby expressly incorporated by reference in their entireties.

FIELD OF THE INVENTION

The invention relates to the field of inhalers for dispensing a medicament for inhalation, e.g. a dry powder or aerosols. Especially, the inhaler relates to inhalers and add-on devices for inhalers capable of determining inhalation flow, and specifically the invention provides an inhaler with a first passive acoustic element for generating sound external to the inhaler, to allow monitoring of inhaled flow, e.g. for monitoring an inhaled medicament dose. Specifically, the first passive acoustic element allows the inhaler to function also for monitoring exhaled air, e.g. for monitoring peak flow.

BACKGROUND OF THE INVENTION

COPD and asthma are examples of lung diseases which require frequent use of inhalation medicaments to improve lung function. However, often the users of inhaler devices do not use the inhalers in the correct manner. E.g. the user does not inhale a full dose of medicament, or the inhalation is not within the prescribed air flow speed. Thus, to ensure correct use, monitoring of the inhalation process can be used to guide the user in correct inhalation behaviour. Further, the users may forget or not be able to take their dose at the prescribed frequency and timing and thereby result in non-adherence or non-compliance.

Inhaler devices exist which are capable of tracking a user's inhalation of medicament, e.g. by means of built-in electrical sensors for sensing inhalation air flow speed, and an associated processor device for processing signals from the sensors accordingly, e.g. so display to the user if an inhalation was successful, or if the air speed was too weak or too strong etc. However, such devices are often expensive and complicated, or they may be complicated to use, e.g. they may require replacement or charging of batteries.

SUMMARY OF THE INVENTION

Following the above, it may be seen as an object of the present invention to provide a simple inhaler that can be used to monitor a user's inhalation of a medicament, in obtaining a desired inhaling air flow speed which can be used in a normal environment. Still further, it would be advantageous to be able to sense the flow rate during inhalation, by a user, employing low cost equipment. Still further, it would be advantageous, if the same device could be used to monitor exhalation function, e.g. monitoring forced exhalation such as determining peak flow.

In a first aspect, the invention provides an inhaler add-on device for add-on to an inhaler for dispensing a medicament to be inhaled, e.g. aerosols or a dry powder, the inhaler add-on device comprising a housing comprising an air inlet, and an air outlet for outputting air to be inhaled by a user, wherein the housing defines a flow path between the air inlet and air outlet, wherein the housing is configured for connection to the inhaler, and a first passive acoustic element arranged in the flow path inside the housing and dimensioned such that air flow passing the first passive acoustic element will generate sound with pre-determined characteristics depending on flow speed of air passing the first passive acoustic element, so as to allow acoustic monitoring of air flow passing the first passive acoustic element external to the housing, wherein the first passive acoustic element comprises a structure having one or more gaps arranged to be passed by an air flow, and wherein the one or more gaps may be shaped and separated by a distance so as to generate sound depending on air flow speed with pre-determined characteristics comprising at least spectral components, e.g. also amplitude. Thus, via designing the passive acoustic element to provide pre-determined distinct characteristics, e.g. spectral peaks, the generated sound allows detection of recognizable characteristics indicative of the air flow, e.g. air flow speed.

Such inhaler add-on device is advantageous, since it has been proven to be possible to provide an inhaler add-on device with a very simple structure, including the passive acoustic element with structured gaps, which allows e.g. 3D printing of the entire inhaler. This allows the inhaler add-one device to be manufactured as a disposable product and/or to be produced at the point of need, e.g. by the user or at a hospital etc. The inhaler add-on device does not require any electrical components inside or on the housing, since the sound is generated by a passive acoustic element, in the same manner as a whistle. Thus, the invention provides a simple low cost add-on device for existing inhalers, either metered dose inhalers, dry powder inhalers or other inhaler types. The sound from the add-on device can be captured by existing processor devices, such as a smart phone with a suitable app. Therefore, the simple add-on device can provide an inhaler user with an important inhalation guidance together with a processor device already at hand. If preferred, the add-on device may in some embodiments include a microphone and connected equipment to perform sound capturing and at least part of the necessary processing to determine, and then communicate data, e.g. via Bluetooth®, to an external device, such as a smart phone, which can then provide the user with inhalation flow information via its display or via an audible message. In some embodiments, the add-on device comprises two separate elements to be attached to an inhaler: one with the passive acoustic element, and one with a microphone to capture sound from the passive acoustic element and equipment to transmit data via Bluetooth® or wi-fi to an external device. Especially, such microphone device may be attached to the inhaler by means of a rubber band around the inhaler. Compared to sound capturing with an external device, such add-on attachment device has a well-defined distance to the sound generating passive acoustic element.

It is based on the insight of the inventors, that a simple passive acoustic element with one or more gaps allows generation of sound with characteristics allowing an external device to capture sound, e.g. a smartphone, and to process the captured sound to allow monitoring inhaled air flow during an inhalation, especially in the important air flow speed range 10-100 litres per minute. In typical embodiments, the sound generated will predominantly be transmitted from the passive acoustic element via the air inlet and since the inhaler can produce a substantial sound pressure, the sound with the important characteristics can be captured by a device having a microphone at a reasonable distance from the inhaler, e.g. at a distance of 1 cm to 1 m, or such as 10 cm to 1 m, or so. This can be achieved by a smartphone, and with the use of a smartphone, data can be stored and e.g. transmitted to doctors and/or hospital etc. Alternatively, a microphone for capturing sound may be part of the inhaler or such microphone may be placed in an inhaler add-on device.

Furthermore, the resulting acoustic information in the sound from the inhaler can also be 1) transferred to a Health app, or a corresponding app on a smartphone (locally), or 2) saved to a central database, cloud or corresponding for further use: including, but not limited to diagnostic, lifestyle monitoring, sport, training, exercise, and social media sharing. The acoustic information can also be used together with some other breath analysis data, i.e. a broad area of analytical sciences covering the analysis of exhaled chemical components in the exhaled air. These can be related to several diseases, including inflammation (asthma), lung cancer, respiratory conditions, but also other diseases.

Especially, it is preferred to track spectral components in the sound generated during inhalation versus time, during an inhalation, and this has been found to be sufficient to monitor air flow speed or an inhaled air volume, e.g. to determine if a full dose of medicament has been inhaled. To do so, a processing algorithm which may be based on pattern recognition and/or machine learning algorithms based on air flow speed tests with a specific implementation of the inhaler, so as to allow the algorithm to determine air flow speed from acoustic characteristics of the sound in the form of amplitude and spectral components, e.g. detection of spectral peaks.

Further, the housing with the flow path and passive acoustic element may be designed as a stand-alone inhaler, i.e. with a mouthpiece at the air outlet. However, in other designs, the housing with the flow path and passive acoustic element can be designed to an attachment, e.g. for click-locking onto, an existing inhaler device, either upstream or downstream of the existing inhaler device.

Even further, the inventors have realized that the inhaler can be used also to monitor exhaled air, e.g. to use it as a peak flow meter for testing the user's lung function. This can be done by either reversing air flow compared to inhalation, i.e. by exhaling into the air outlet, or by exhaling into the air inlet. A second passive acoustic element to be used only in exhalation mode may be used. By capturing sound generated by the passive acoustic element in this exhalation mode e.g. by forced exhalation, it is possible to determine one or more parameters indicative of the user's lung function. This is an important feature of the inhaler, since the user then only needs one single device for medication as well as to test the lung function, which is important in the correct medication of a lung disease.

In both inhalation and exhalation mode of operation, a smartphone or equivalent device with a processor and a microphone can be used as an external device for capturing sound from the inhaler and performing the necessary signal processing. Thus, in general no extra, complicated and dedicated equipment is needed for the user to monitor inhalation and exhalation. Further, by using a smartphone or equivalent, the user can communicate the results to a medical doctor or hospital.

In the following preferred features and embodiments will be described. It is to be understood that the acoustic features of an inhaler add-on device may be built together with or integrated with an inhaler. Thus, in the following, even by referring to an inhaler, the general features and embodiments described will apply for such inhaler as well as the specific embodiments implemented as an inhaler add-on device for add-on to an existing inhaler.

The first passive acoustic element is preferably a non-vibrating structure arranged to generate sound by movement of air passing the passive acoustic element.

Preferably, the one or more gaps of the acoustic element are such as 0.5-3 mm wide. The length of the gap(s) may be such as 2-10 mm. Material thickness around the gap(s) is preferably 0.5-3 mm. Preferably, the gap(s) have rather sharp edges, such as edges formed by 90° corners, or at least corners of such as 40°-140°, or such as 70°-110°. E.g. this can be obtained in a manufacturing process by 3D printing the passive acoustic element with a 3D printing resolution better than such as 200 µm, preferably better than 100 µm. The inhaler is suited to be 3D printed, since it is possible to print it monolithically in spite of a rather complex inner geometry, including the passive acoustic element with structured gaps to produce the acoustic output. The gap(s) may be rectangular in shape with a length of 2-5 times the width. Alternatively, the shape may have a length of 2-5 times the width, having two parallel walls, but with one tapered end. Especially, the passive acoustic element may be formed as one or two rows of substantially rectangular shaped parallel gaps, each having a length of at 2-5 times the width.

Preferably, the air flow direction for air passing the gap(s) is perpendicular to a length axis of the gap(s).

Especially, the one or more gaps may be shaped and separated by a distance so as to generate sound depending on flow speed with pre-determined characteristics comprising at least one spectral peak, or two to four spectral peaks. The sound may vary in dependence of air flow speed by variation in amplitude and/or frequency of such spectral peaks. Spectral peaks (pure tones) in the sound are rather easy to detect even in a noisy environment, thus allowing practical use of the inhaler without requiring especially quiet environments.

The first passive acoustic element may have surfaces in or adjacent to the one or more gaps which have surface morphology (e.g. in micro meter scale, "micro-structuring") and surface material, which can both be selected depending on the type of gap(s) selected and which specific sound is preferred. In other words, the "micro-structure" of the various surfaces of first acoustic element will influence the air flow around the gap(s) and thus also the generated sound.

The first passive acoustic element may be designed to generate sound predominantly within an audible level and in an audible frequency range, thereby allowing the user to hear tones indicative of inhalation air flow speed. It may alternatively be preferred to design the first passive acoustic element so as to generate sound predominantly with frequencies above 14 kHz, so as to be generally inaudible, thus allowing the inhaler to be used in public without generating any offensive or disturbing tones. Still further, the first passive acoustic element may be designed to generate sound with audible and inaudible spectral components for air flow speeds in the relevant range for inhalation.

The flow path and the passive acoustic element are preferably designed so as to generate sound with detectable pre-determined characteristics for air flow speeds at least within the interval 20-90 litres per minute, preferably within the interval 10-100 litres per minute, thereby allowing processing of relevant inhalation air flow speeds of a human user. This has been proven possible by the inventors with rather simple designs, even to allow individual adaptation of the passive acoustic element to the lung capacity of the user.

In preferred embodiments, the first passive acoustic element has a plurality of gaps, e.g. 2, 3, 4, 5 or more gaps, which are separated by a distance (seen in the direction of air flow), e.g. the first passive acoustic element may have a plurality of sets of gaps separated difference distances. E.g. the first passive acoustic element may have a plurality of gaps with identical heights and lengths, and/or a plurality of gaps with different heights and lengths. Especially, the one or more gaps may be straight gaps which are perpendicular or substantially perpendicular to a direction of air flow passing the first passive acoustic element.

In preferred embodiments, the first passive acoustic element comprises a structure having teeth defining one or more gaps between them, wherein the one or more gaps being a passage through the structure with no material being present in the gap. Especially, the gaps are a series of gaps defined within a hollow structure guiding the air flow. The hollow structure may especially have plane upper and lower parts, and air flow is guided parallel with these upper and lower plane parts.

At least one tube element may be arranged inside the housing and having one end connected to the air inlet or air outlet, e.g. two or more tube elements may be arranged inside the housing and forming part of the flow path to let air flow pass the first passive acoustic element.

In some embodiments, the air inlet is arranged at a bottom part of the housing, wherein the air outlet is arranged at a top part of the housing. Especially, the first passive acoustic element may be arranged so between the air inlet and air outlet, that a direction of air flow passing the first passive acoustic element is perpendicular to or substantially perpendicular to a direction of air entering the air inlet. Especially, the first passive acoustic element may be arranged so between the air inlet and air out, that a direction of air flow passing the first passive acoustic element is perpendicular to or substantially perpendicular to a direction of air exiting the air outlet.

The first passive acoustic element can be positioned in the flow path upstream or downstream of an inhaler medicament compartment for providing medicament to be inhaled. Especially, the medicament compartment may be a multi dose chamber or capsule, or a single dose chamber or capsule. As an alternative, the first passive acoustic element and an inhaler medicament compartment for providing medicament to be inhaled are arranged in respective parallel flow paths. E.g. the air inlet is split into two separate openings each guiding air to the respective parallel flow paths. This allows freedom to design the flow path around the passive acoustic element irrespective of the inhalation flow path. Breaking a capsule by a mechanism (small needle) inside the inhaler to allow inhaling the medicament from the capsule, and this process will also make a sound, which can be used to detect, whether the capsule was fully functional and/or properly stored. Thus, further analysis of sound from the inhaler may be used to provide additional information regarding the use of the inhaler.

A second passive acoustic element may be positioned at a different location inside the flow path than the first passive acoustic element. Hereby, additional sound components or characteristics can be generated, e.g. for facilitating the processing of sound to arrive at a measure of air flow speed.

In some embodiments, the inhaler is arranged for positioning of an inhaler medicament capsule inside the housing, so as to allow inhaling a mixture of air and medicament released from the said capsule via the air outlet. Especially, the inhaler is arranged to be opened and closed by a user's hand or hands, so as to allow insertion and replacement of an inhaler medicament capsule, e.g. a top part of the housing may be arranged for being taken off and put back on by the user.

In some embodiments, the inhaler is a multi dose disposable inhaler which is manufactured with multiple medicament doses inside the housing, and when all doses have been inhaled, the inhaler can be discarded. Such embodiment may be designed so that it cannot be opened by the user, i.e. without any tools. In some embodiments, the housing and the first passive acoustic element is formed as a monolithic element, such as formed as one single polymeric material.

In embodiments, the air inlet or air outlet of the housing is arranged for connection to a separate device, wherein said separate device comprises a compartment comprising a medicament to be inhaled. I.e. in such embodiments, the housing and passive acoustic element etc. therein is an add-on to an existing inhaler device, e.g. reusable or non-reusable inhaler, that being single dose or multi dose devices.

Specifically, in an inhaler add-on embodiment, the housing has a mouth piece in one end, and a fitting part at the opposite end, wherein the mouth piece is arranged for contact with the user's mouth during inhalation, and wherein the fitting part is arranged for connection to the inhaler by attachment of the fitting part to an air outlet of the inhaler. E.g. the fitting part may be arranged to lock a position of the inhaler add-on device to the inhaler. Specifically, the fitting part may be shaped so as to receive an air outlet pipe of the inhaler and to allow locking of the position of the inhaler add-on device to the inhaler upon insertion of the outlet pipe of the inhaler into the fitting part of the inhaler add-on device. The fitting part may have other means for attachment to the inhaler, e.g. using a magnet, protrusions/indentations serving for click locking etc. The mouth piece may have a first outer cross sectional area, and wherein the fitting part has a second outer cross sectional area being larger than the first outer cross sectional area of the mouth piece. In this way the add-on device is shaped to provide a tight fit when pressed onto the inhaler. Specifically, the mouth piece may have a circular or elliptical outer cross sectional shape.

The housing of such inhaler add-on device may be shaped to provide a straight flow path between the mouth piece and the fitting part. Specifically, the first passive acoustic element may be arranged inside the mouth piece and with one opening connected to the opening of the mouth piece, wherein an opposite opening of the first passive acoustic element is connected to a flow path inside the housing. If preferred the first passive acoustic element may be placed inside the housing in an intermediate part of the housing between the mouth piece and the fitting part of the housing.

In an inhaler add-on embodiment, the first passive acoustic element is arranged in a flow path so as to receive a limited part of an air flow through the mouth piece. E.g. such limited part of the air flow may be such as 2-80%, such as 5-50%, such as 10-30%, of an air flow through the mouth piece. Hereby, the passive acoustic element can be kept away from the main flow of medicament, which can be advantageous. Further, the lower flow that needs to pass the acoustic element can be advantageous. Specifically, the first passive acoustic element may be arranged in an air flow path between an opening of the housing and air flow inside the housing, wherein the opening of the housing is separate from the mouth piece and the fitting part. Specifically, the first passive acoustic element may be arranged in a flow path with a direction which is perpendicular to a flow path direction in the mouth piece.

An inhaler add-on embodiment comprises a second passive acoustic element with one or more gaps shaped and separated by a distance so as to generate sound depending on air flow speed with pre-determined spectral component characteristics. Specifically, the second passive acoustic element may be arranged to provide spectral component characteristics different from the first passive acoustic element.

In an inhaler add-on embodiment, the mouth piece may be arranged to receive exhaled air, so as to allow acoustic monitoring of exhaled air flow external to the add-on device upon a user exhaling air into the mouth piece.

In such an inhalation and exhalation embodiment, a first passive acoustic element may be arranged to generate sound in response to inhaled air flow through the mouth piece, and a second passive acoustic element may be arranged to generate sound in response to exhaled air flow through the mouth piece, i.e. using two separate passive acoustic elements. However, it is to be understood that in principle, the first and second passive acoustic elements may be identical with respect to their structure. It may be preferred that their structures are different, since the flow speed to be measured during inhalation and exhalation can be expected to be different. In a specific embodiment, a first valve is arranged to block exhaled air flow from passing the first passive acoustic element, and a second valve arranged to block inhaled air flow from passing the second passive acoustic element. This would further ensure that air flow does not go in the wrong direction in the add-on device and inhaler and also ensures that the user does not exhale into the inhaler, which may otherwise damage the medicine inside the inhaler Specifically, the first and second passive acoustic elements and the first and second valves may be arranged in the mouth piece.

In an inhaler add-on embodiment, a microphone is arranged to capture sound from the first acoustic passive element, and the embodiment is further being arranged to transmit data in response to captured sound by means of a wired or wireless connection to an external device, such as a smart phone or other mobile device. Specifically, the microphone, a processor circuit connected thereto is arranged to transmit said data, and a battery for powering the processor circuit are housed in a second housing separate from the first housing, preferably the second housing is arranged for attachment to the inhaler. Thus, in this embodiment, two separate add-on components are to be attached to the inhaler, e.g. the sound generating add-on device to be attached to the outlet pipe of the inhaler, while the sound capturing add-on device is to be attached to another part of the inhaler, e.g. via a rubber band etc. E.g. a Bluetooth® connection to a mobile device, e.g. a smart phone, may be used to transmit recorded sound to the mobile device for further processing. E.g. the processor circuit is programmed to perform all of or at least a part of processing required to determine inhalation flow speed in response to the captured sound.

In some embodiments, the inhaler is further arranged to receive exhaled air via the air inlet or the air outlet, so as to generate sound with pre-determined characteristics depending on flow speed of air passing the first passive acoustic element, so as to allow acoustic monitoring of air flow passing the first passive acoustic element external to the housing upon a user exhaling air into the air inlet or air outlet. Thus, this adds another functionality utilizing the passive acoustic element of the inhaler to generate sound also during exhalation, thereby allowing lung function tests, e.g. FEV1 or peak flow measurement etc. E.g. this allows making a flow-volume profile using both the inhaled and exhaled volumes and flow rates. Especially, the inhaler may comprise a second passive acoustic element separate from the first passive acoustic element, serving to generate sound upon air being exhaled into the air inlet or air outlet. Specifically, the inhaler may be arranged to receive exhaled air through the air outlet, and wherein the flow path comprises a valve mechanism arranged to guide exhaled air from the air outlet via the second passive acoustic element and to the air inlet. In other implementations, the inhaler is arranged to receive exhaled air via the air inlet.

The first passive acoustic element can be formed as a monolithic part of the housing, if preferred. In some versions, the first passive acoustic element is formed as a monolithic part of a bottom part of the housing. Alternatively, the first passive acoustic element may be a separate element attached to an inner structure of the housing, thereby allowing the housing and flow path elements to be re-used in several versions, where only the passive acoustic element itself is replaced to provide special acoustic characteristics, e.g. suited to specific needs of specific users.

E.g. the housing and passive acoustic element may be formed by a polymeric material. In some versions, the inhaler is a disposable product, such as being manufactured with a medicament positioned inside the housing.

The inhaler may comprise a second air inlet or a second air outlet of the housing. Especially, in versions suitable for exhalation, a separate air outlet may be provided to guide air out of the housing during exhalation.

Further sound from the inhaler, i.e. not generated by the passive acoustic element, can be analysed to provide further information regarding the use of the inhaler, e.g. to establish if a medicament dose has been correctly inhaled. E.g. such sound may be sound from the perforating or opening of a medicament container (capsule) inside the inhaler for preparing an inhalation dose.

Even though described as a simple inhaler structure, e.g. for disposable products, it is to be understood that more refined versions of the inhaler may be designed to be user for inhalation and/or exhalation at high precision.

In a second aspect, the invention provides a computer program product being adapted to enable a computer system comprising at least one computer having data storage means in connection therewith to control a manufacturing system or device, preferably an additive manufacturing system or device or a three-dimensional (3D) printing system or device, for producing an inhaler or inhaler add-on device according to any of the preceding claims. Such program product may be present on a tangible medium and/or on a net based platform arranged for downloading. Especially, 3D printing may facilitate a personalization of the inhaler or inhaler add-on device. It may be possible, e.g. using software design tools, to influence one or more parameters of the first acoustic element and the gap(s) thereof, so as to personalize the sound generate to match individual needs of the user. E.g. to ensure content of low frequency tones to a user who is high frequency hearing impaired.

In a third aspect, the invention provides a system comprising an inhaler add-on device according to the first aspect, and
a device, such as a smart phone, arranged to capture sound generated by the inhaler add-on device during an inhalation, wherein the device comprises a processor arranged to process the captured sound according to a processing algorithm and to generate a measure of air flow through the air outlet of the inhaler in response to the processing algorithm.

Especially, the processing algorithm may be arranged to determine whether a planned medical dose has been taken correctly, e.g. to determine if a medicament capsule is empty or not. Further, as mentioned, analysing sound generated by pinning the capsule, it is possible to determine if the capsule was correctly perforated, and if it was in a good condition, e.g. had been correctly stored. The device may display or provide audible output to the user accordingly, and/or transmit a message to an external party accordingly.

Especially, the algorithm comprises performing a spectral analysis of the captured sound. E.g. the algorithm may comprise performing a noise suppression part for suppressing undesired background noise. E.g. the processing algorithm may comprise performing a pattern recognition part, e.g. to determine lung performance, diagnosis, improved condition before and after treatment, or daily variations in lung function (day/night) etc. The processing algorithm may be arranged to determine a measure of air flow and to compare this air flow to a predetermined reference value, so as to determine if a medical dose has been inhaled according to predetermined conditions, such as to determine if a predetermined medical dose has been inhaled. The processing algorithm may be designed in accordance with the design of the first passive acoustic element and the design of the flow path, so as to allow the processing algorithm to generate a measure of air flow speed in response to the captured sound. Especially, the processing algorithm may be designed to generate a measure of air flow speed versus time for at least a major part of an inhalation, in response to the captured sound. Sound captured during an inhalation or exhalation using the inhaler may be processed versus time, such as processed in time segments each having a length of such as 1 ms to 500 ms.

In a fourth aspect, the invention provides a method for measuring inhaled flow in an inhaler add-on device according to the first aspect, the method comprising
  capturing sound external to the housing generated by the inhaler add-on device during a user inhaling a medicament through the air outlet of the inhaler,
  processing the captured sound according to a processing algorithm, and
  generating a measure of inhaled air flow, such as a measure of inhaled air volume and/or flow speed, through the air outlet of the inhaler add-on device in response to the processing algorithm.

In a fifth aspect, the invention provides a computer executable program code arranged to cause a device to perform the method according to the fourth aspect, when executed on a processor. This may be in the form of a downloadable application (app) for a smartphone etc. Especially, the processing or at least a part of the processing may be cloud based. I.e. a cloud performs processing fully or partially, an evaluation and storing of data from the inhalations. Hereby, it is not required to install software for data processing on the users' device, e.g. smartphone.

BRIEF DESCRIPTION OF THE DRAWINGS

Embodiments of the invention will be described, by way of example only, with reference to the drawings, in which
FIGS. 2-6 show various inhaler embodiment.

DESCRIPTION OF EMBODIMENTS

Figure 1:
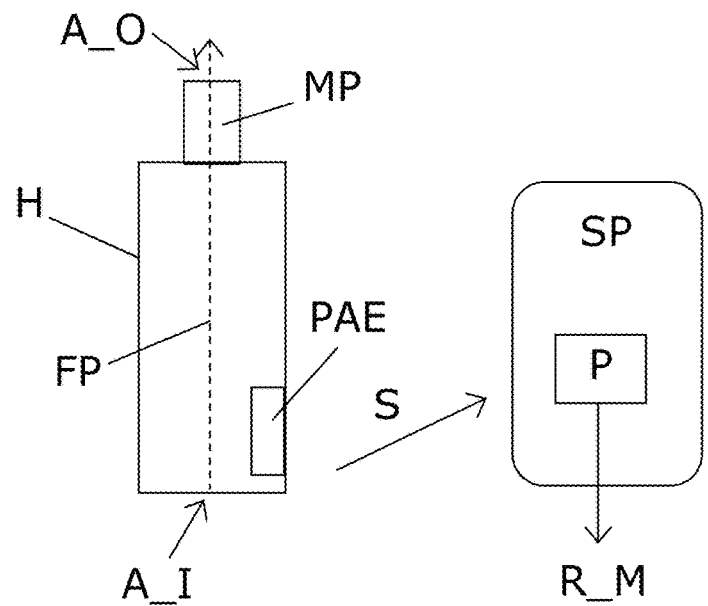
FIG. 1 illustrates a system embodiment.

FIG. 1 shows a block diagram of an inhaler system embodiment with a sketch of an inhaler for dispensing a medicament to be inhaled. The inhaler has a housing H with an air inlet A_I on its bottom part, and an air outlet A_O with a mouthpiece MP for outputting air to be inhaled by a user. The housing H forms a cavity within an outer wall. Inside this cavity, the housing H defines a flow path FP between the air inlet A_I and air outlet A_O. A passive acoustic element PAE is arranged in the flow path FP inside the housing H and dimensioned such that air flow passing it will generate sound S with pre-determined characteristics depending on flow speed of air passing the passive acoustic element. This allows acoustic monitoring of air flow passing the first passive acoustic element external to the housing H, namely by an external device SP, such as a smartphone. The passive acoustic element PAE comprises a structure having one or more gaps arranged to be passed by an air flow in order to generate the sound S, in the shown version sound S which predominantly exits the air inlet A_I.

The smartphone SP is arranged to capture sound S generated by the inhaler during an inhalation via its built-in microphone. By an application program, the smartphone processor P is arranged to process the captured sound S according to a processing algorithm and to generate a result in the form of a measure of air flow R_M through the air outlet A_O of the inhaler in response to the processing algorithm. With such output R_M, the user or other, can be informed e.g. on the display of the smartphone SP about the quality of a medicament inhalation, e.g. to determine if a dose of medicament has been inhaled correctly e.g. using visual symbols, such as a green color, a happy face etc. Alternatively, the output R_M may be in the form of an audible signal, e.g. to indicate that a full medicament dose has been successfully taken.

Figures 2A, 2B:
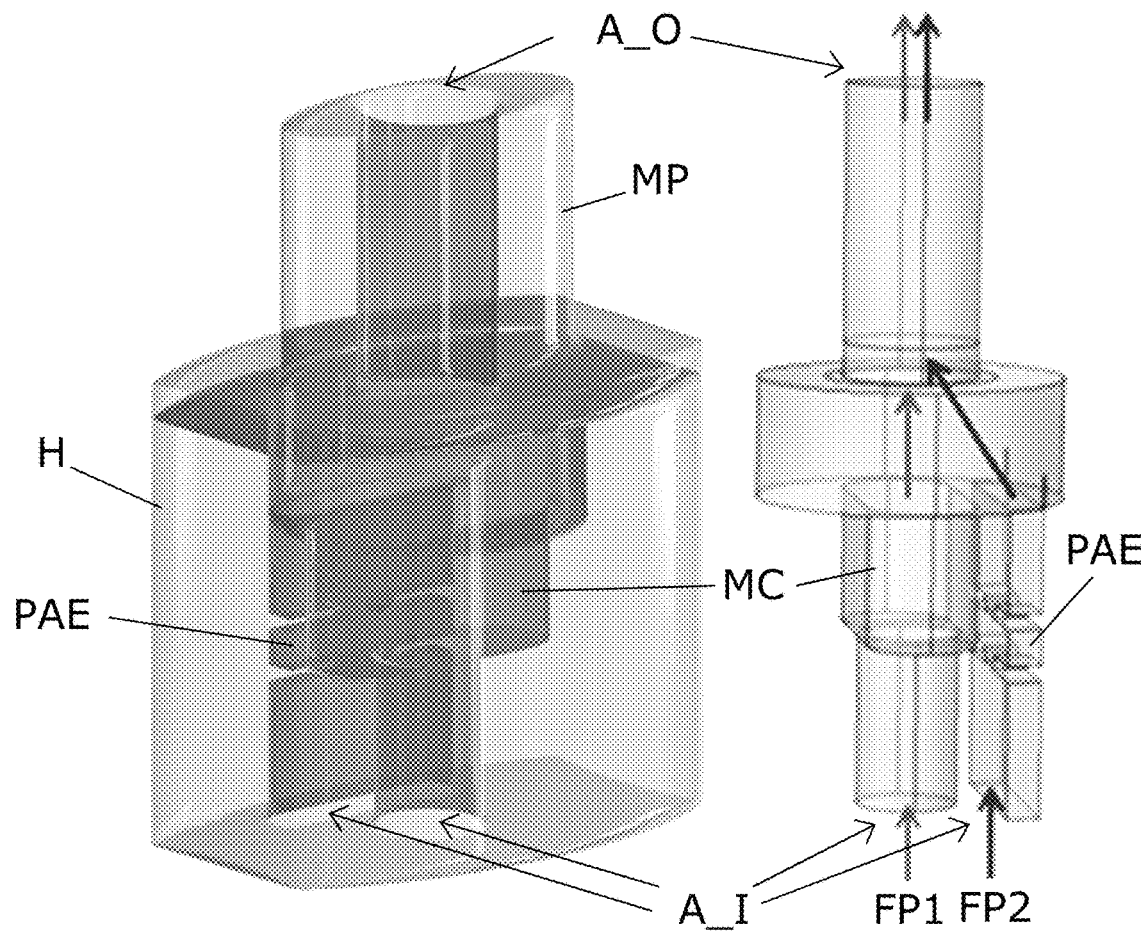

FIGS. 2a and 2b show sketches of a stand-alone inhaler embodiment arranged for having a medicament compartment or capsule MC arranged inside the housing H. FIG. 2a shows a transparent drawing, while FIG. 2b shows only inner part of the housing H with arrows indicating parallel flow paths FP1, FP2 each having their air inlet A_I openings on the bottom of the housing H both ending at the mouth piece MP forming the air outlet A_O. One flow path FP1 has a tube connecting the air inlet A_I with a medicament capsule MC, and another tube connects the medicament capsule MC with the air outlet A_O. Another flow path FP2 connects the air inlet A_I with the passive acoustic element PAE arranged on a side wall inside the housing H, and it has two gaps separated by a distance. Thus, air flow is guided to pass the two gaps of the passive acoustic element PAE in a direction parallel with a centre line through the air outlet A_O. The housing H may be formed by a polymeric material, e.g. 3D printed, however other materials may be used as well.

A mixture of air from the two flow paths FP1, FP2 is thus guided to the mouthpiece MP allowing the user to inhale medicament from the medicament capsule MC, thus generating sound with pure tone components depending on the air flow speed of the flow path FP2, but also depending on air flow speed of the flow path FP1 through the medicament capsule MC. Thereby, it is possible to determine the air flow speed of the flow path FP1 via the medicament capsule MC and thus the medicament dose delivered during an inhalation via the air outlet A_O.

In other embodiments, the inhaler has no mouthpiece MP, but instead the air outlet A_O can have an interface arranged for connection to the air inlet of an existing inhaler device. In still another embodiment, the inhaler has a mouthpiece MP, but the air inlet A_I is designed to interface an air outlet of an existing inhaler device.

FIG. 3 shows interior part of an alternative to the embodiment of FIGS. 2a and 2b with the same type of passive acoustic element PAE, but here it is located in the flow path FP upstream of the medicament compartment MC, namely with the passive acoustic element PAE positioned at a bottom part of the housing (not shown here for simplicity).

FIG. 4 shows interior part of still another alternative to the embodiment of FIGS. 2a and 2b with the same type of passive acoustic element PAE, but here it is located in the flow path FP downstream of the medicament compartment MC, namely inside a tube leading air to the air outlet.

Figure 5C:
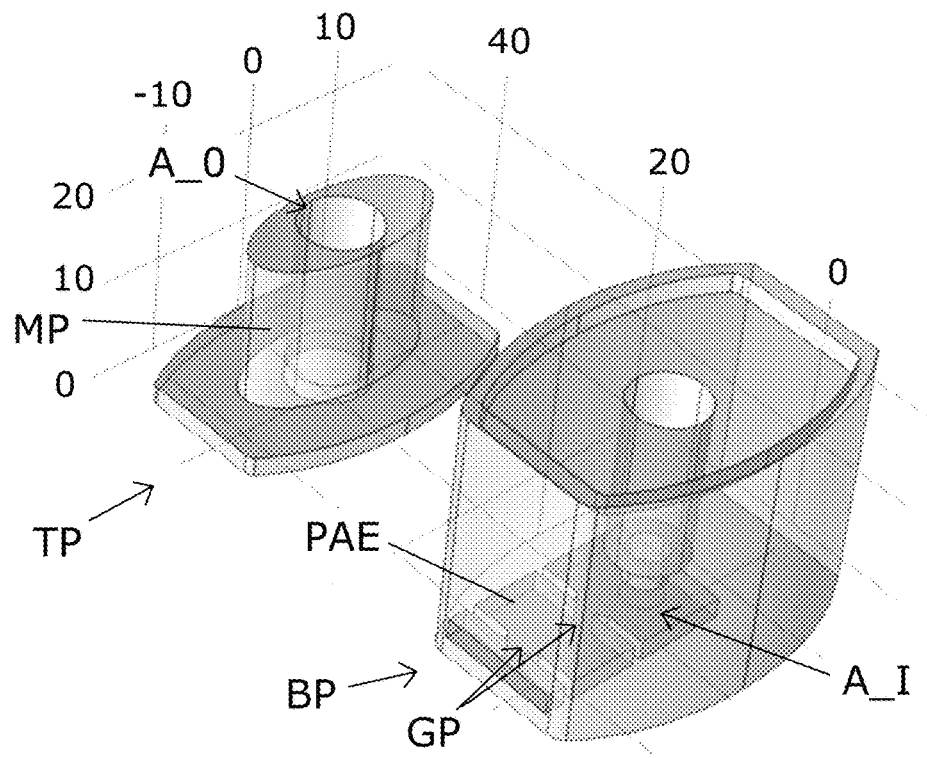

FIGS. 5a-5c show different transparent views of an inhaler embodiment with a preferred type of passive acoustic element PAE having two sets of gaps in series and with dimension lines with values in mm indicated. FIGS. 5a and 5b show the lower part of the housing H only with the air inlet A_I at a bottom part, whereas FIG. 5c shows the housing H being split into a bottom part BP including walls forming a cavity with the passive acoustic element PAE inside, and with an upper opening allowing the user to split the inhaler by hands for insertion of a medicament capsule or the like. A top part TP has a shape matching to close the opening of the bottom part BP, and on its top, the top part TP has a mouthpiece MP, thus forming the air outlet A_O of the inhaler. It is also possible to make different open/closing mechanisms to separate the inhaler's two parts. E.g. such mechanism can be a screwing mechanism, a sliding mechanism, or a click lock mechanism.

The passive acoustic element PAE is having: a gap GP being a passage through the passive acoustic element PAE with no material being present in the gap GP. In the shown specific embodiment, two gaps GP are separated by a distance of D2, e.g. 8 mm, and each gap GP has a width D1, e.g. 2 mm. The height D3 of the gaps GP may be such as 0.5-3 mm, however preferably 1-2 mm. The length D4 of the teeth defining the gap GP in the shown embodiment is such as 5 mm, wherein a width D5 of each tooth is such as 2 mm. Especially, the structure of the passive acoustic element PAE may be a monolithic hollow structure forming a flow path to guide air flow to pass the gaps GP.

It is to be understood that all indicated dimensions D1-D5 can be tuned individually in order to shape the sound generated.

The passive acoustic element PAE can be formed monolithically, e.g. monolithically as a part of the housing H, or it can be manufactured, e.g. 3D printed separately, thus allowing freedom of acoustic design. This may allow a medical doctor to design the passive acoustic element PAE to match the lung capacity and/or hearing capacity of the user (patient) to use the inhaler. Hereby optimal adaptation to the individual user can be obtained, thus facilitating that the user can learn to hear the sound from the inhaler and inhale accordingly, also in case the user has a limited high frequency hearing capacity. It may alternatively be preferred to injection mold the inhaler, or to 3D print certain parts of the inhaler, while other parts are injection molded.

Figure 6:
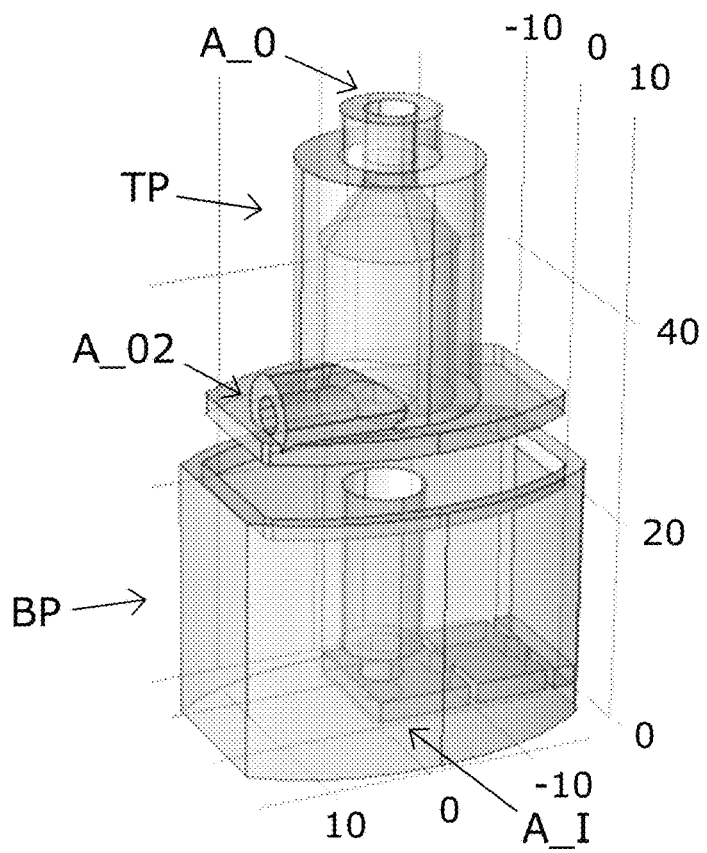

FIG. 6 shows another inhaler embodiment, where the bottom part BP is the same as in FIGS. 5a-5c, but where the top part TP has a second air outlet A_O2 which is connected to the interior cavity of the housing H. In the shown embodiment, the tube connecting the second air outlet A_O2 to the interior cavity of the housing H is perpendicular to a central axis through the air inlet A_I and the first air outlet A_O.

The top part TP allows the inhaler to also function as a sound frequency dependent exhale, namely where the air outlet A_O can be used for inhalation as well as exhalation, e.g. to allow testing of the user's lung function. A valve mechanism may be used to ensure that exhalation air outlet is only performed via second air outlet A_O2.

The embodiment shown in FIGS. 5a-5c could as well be used for exhalation by reversing it, or by adding a separate channel for exhalation, depending on preference.

In the following, results of sound spectra for various inhaler embodiments under various conditions will be described.

The influence of the number of gaps on the passive acoustic element in the inhaler has been tested to demonstrate that a certain number of gaps are preferred to generate a sound, i.e. an acoustic signal, which has characteristics which correlate to air flow speed.

Figure 7A:
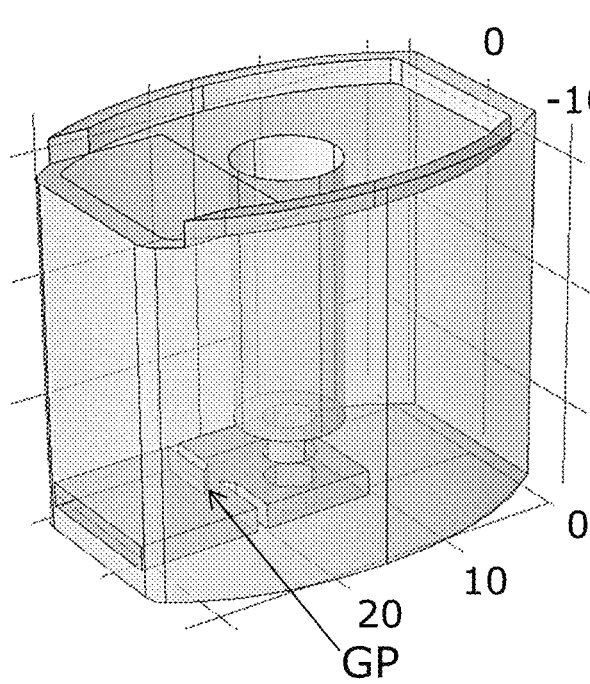
FIGS. 7-10 show various inhaler embodiments with different gap configurations of their passive acoustic element along with the produced sound spectra,
  FIGS. 11-12 indicate sound produced by a high and low resolution 3D printed version of one inhaler embodiment.
Figure 7B:
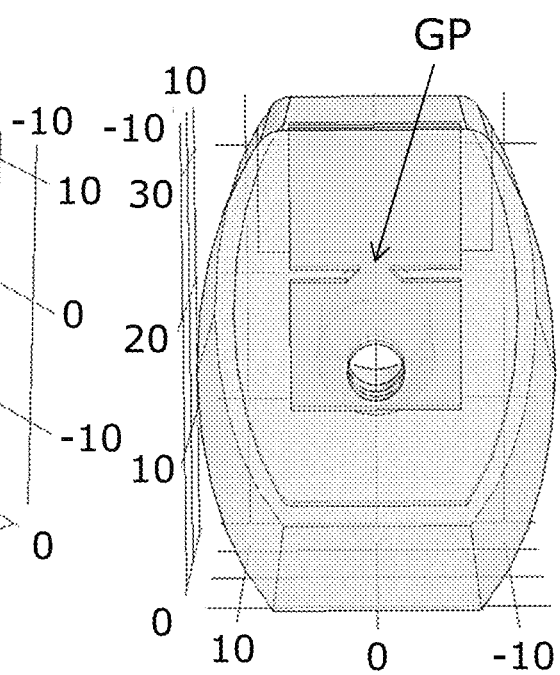

FIGS. 7a and 7b show an inhaler housing bottom part similar to the embodiment of FIGS. 5a-5c, but here with a passive acoustic element having only one gap GP.

Figure 7C:
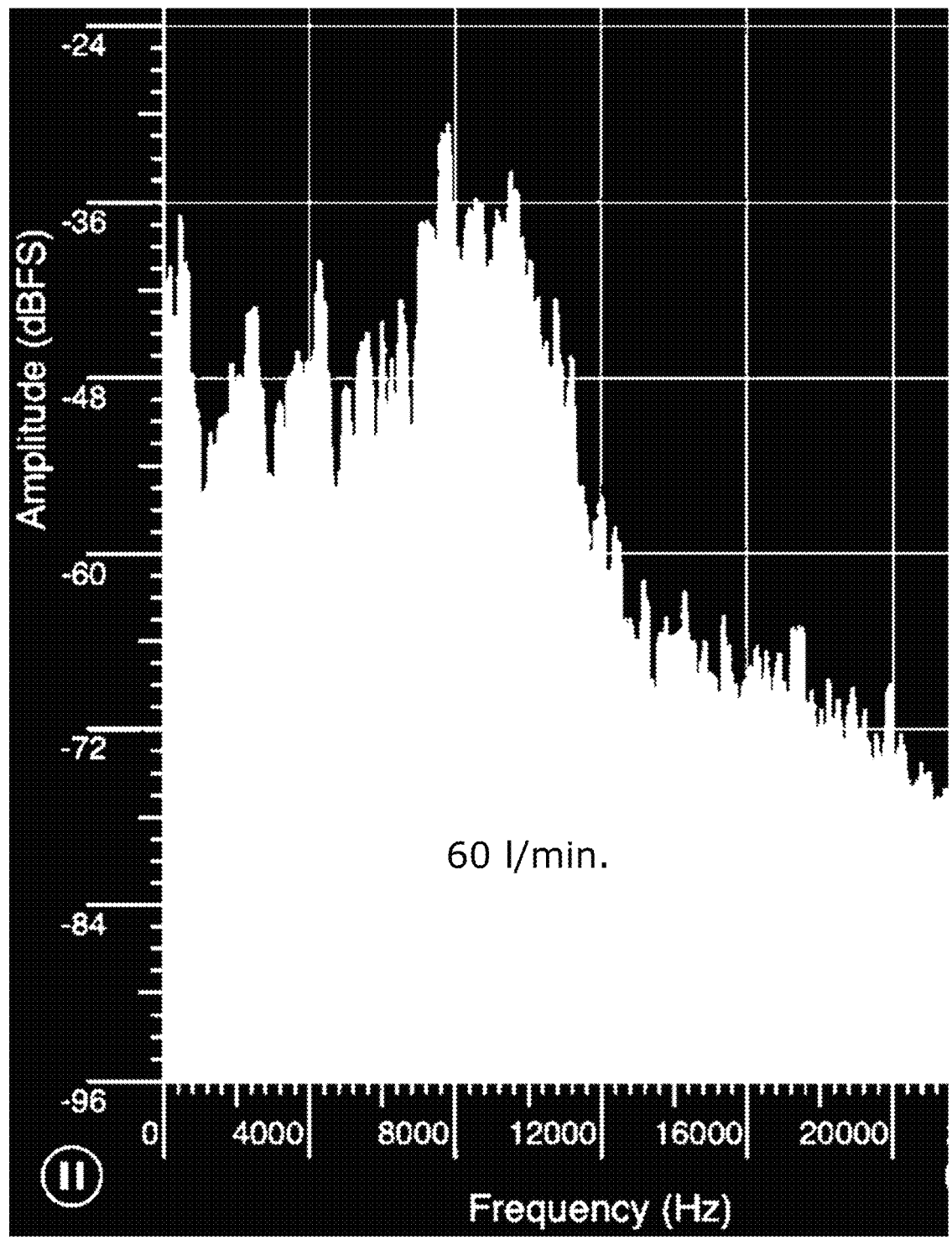
Figure 7D:
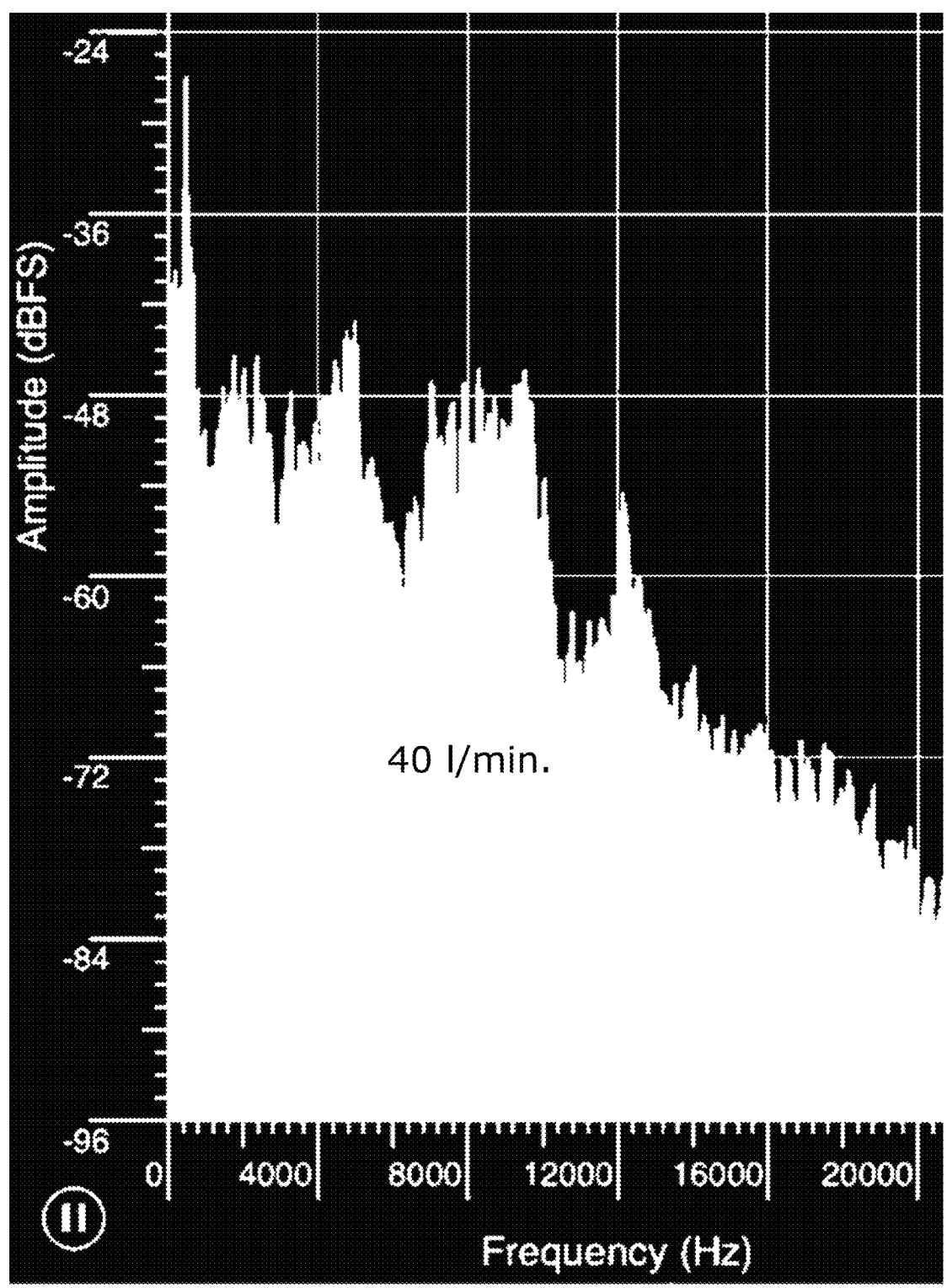

FIGS. 7c and 7d illustrate sound spectra at an inhalation air flow speed of 60 l/min. and 40 l/min. for the embodiment of FIGS. 7a and 7b. The sound spectra for the two are clearly different, but without clear and distinct peaks indicating clear pure tone components, which are easy to identify with appropriately selected signal processing algorithms.

FIGS. 8a and 8b show again an inhaler as in FIGS. 7a and 7b, but here with two gap GP in series and separated by a distance (D2 referring to FIGS. 5a, 5b) of such as 8 mm. The shape and size of each single gap GP is identical with the gaps in FIGS. 7a and 7b.

Figure 8A:
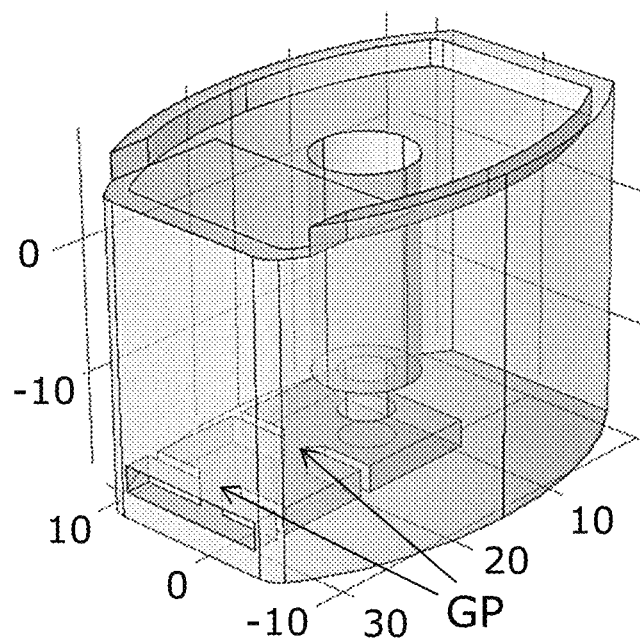
Figure 8B:
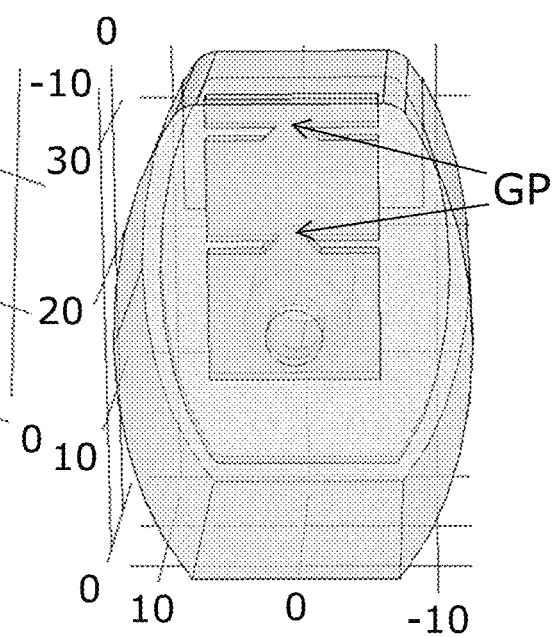
Figure 8C:
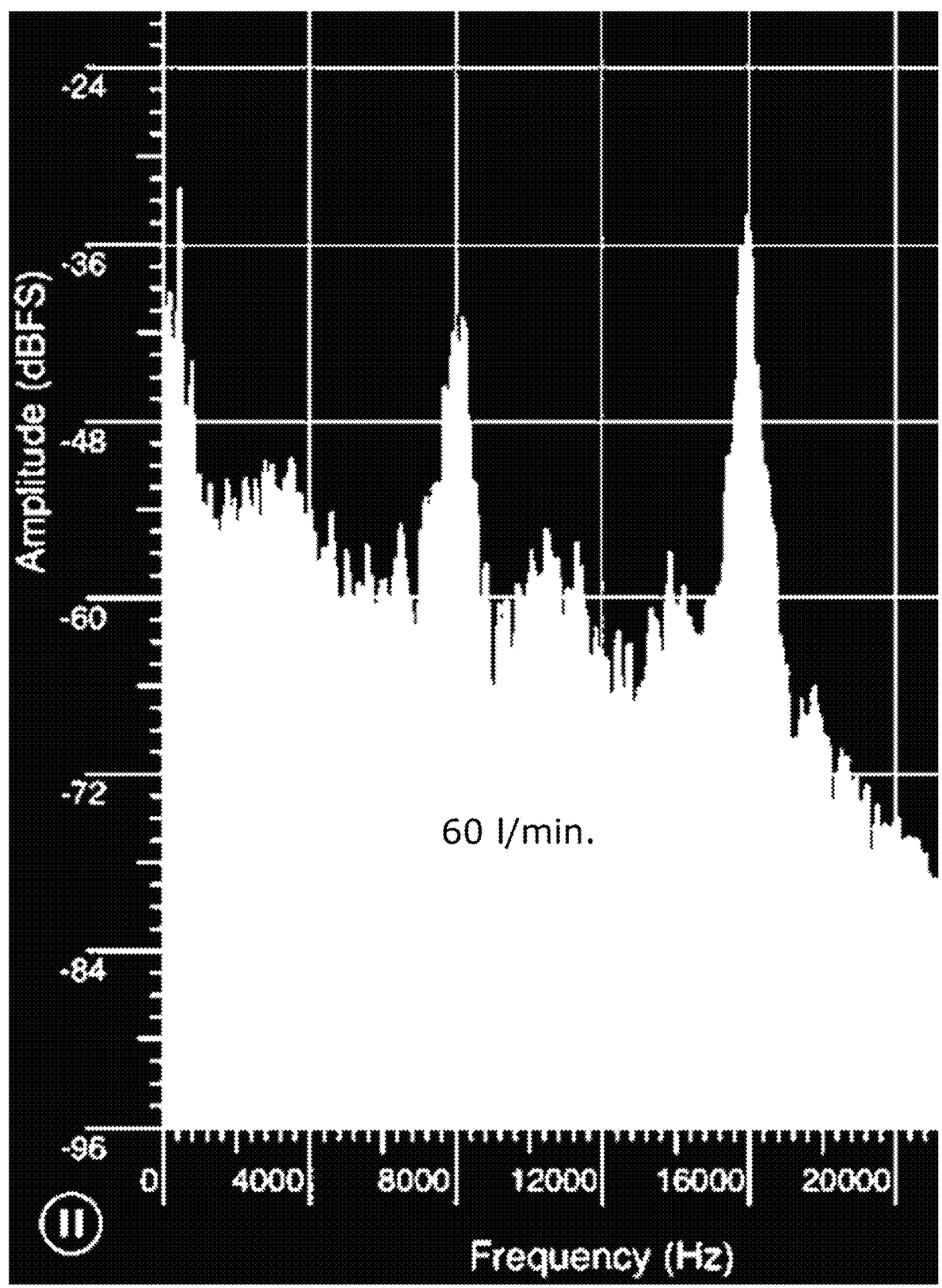
Figure 8D:
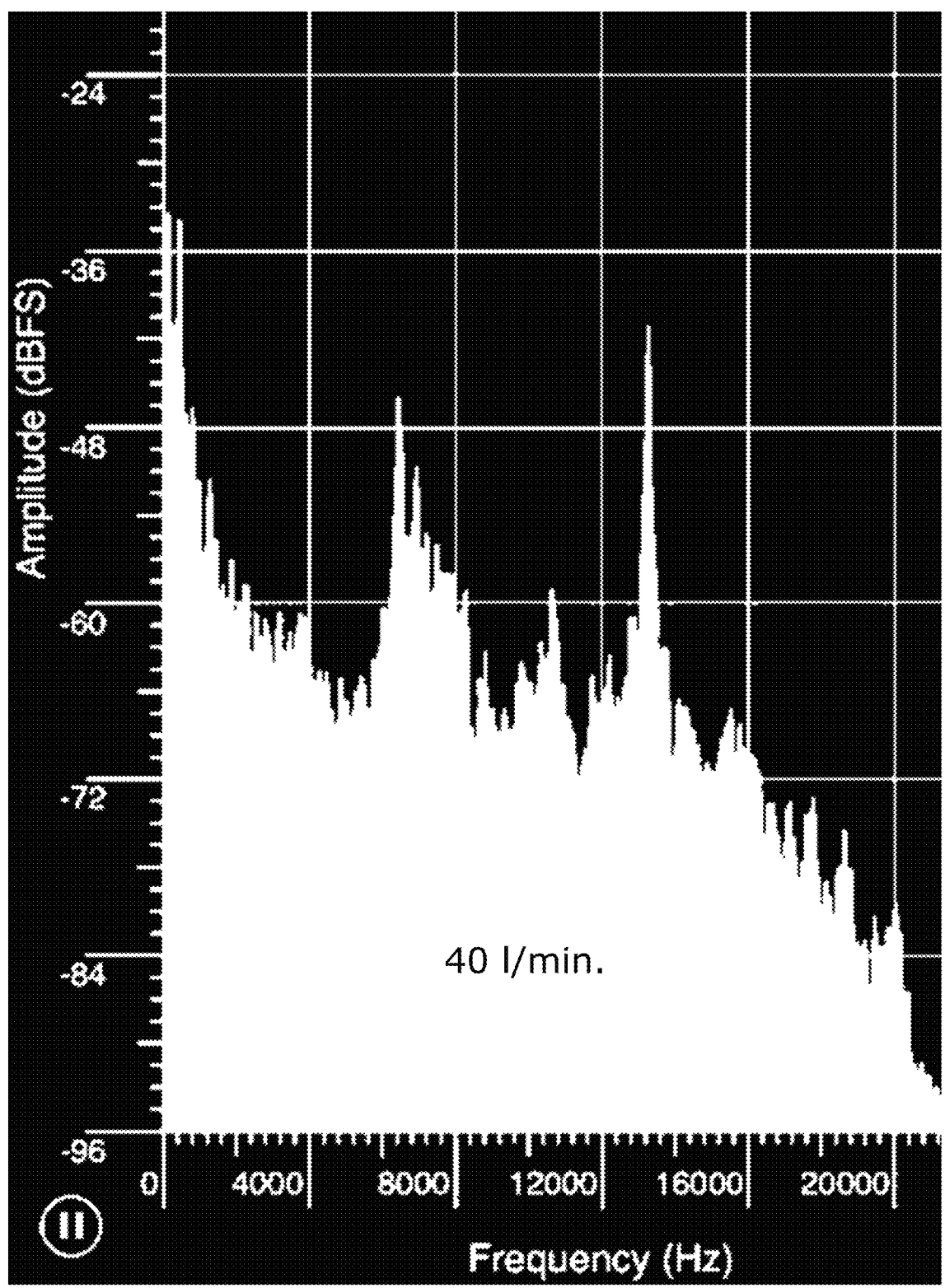

FIGS. 8c and 8d illustrate sound at an inhalation air flow speed of 60 l/min. and 40 l/min. for the embodiment of FIGS. 8a and 8b. Two clear narrow spectral peaks are seen at 8 and 16 kHz at air flow speed 60 l/min., whereas corresponding peaks at 40 l/min. are located at about 6.5 and 13 kHz. Thus, this embodiment with two gaps GP allows easy spectral correlation to air flow speed. It is to be used that more gaps GP in series than two may be used, e.g. 3, 4, 5, if preferred. The overall sound pressure level, i.e. the amplitude, is similar for the embodiments in FIGS. 7 and 8, but due to the narrow spectral peaks in the sound signal, two sets of gaps are preferred.

Figures 9A, 9B:
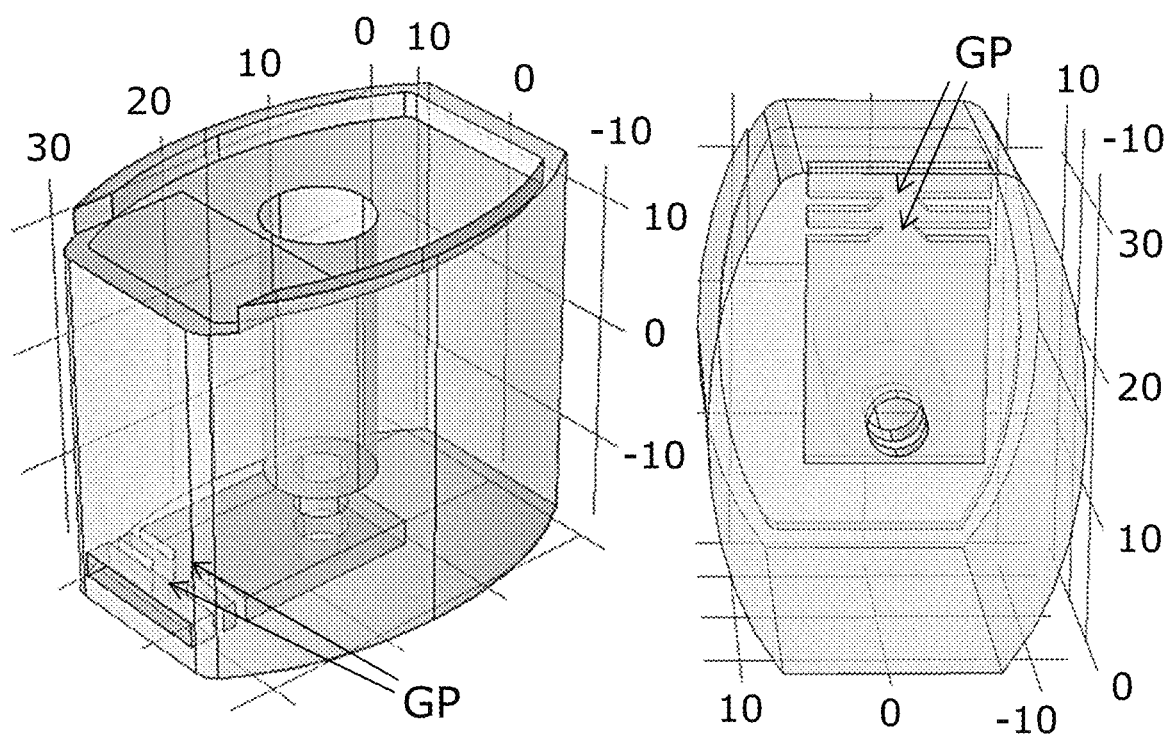

FIGS. 9a and 9b show an inhaler similar to FIGS. 8a and 8b, but here with the passive acoustic element having the two gaps GP in series separated by a shorter distance (D2 referring to FIGS. 5a, 5b), namely such as 2 mm.

Figure 9C:
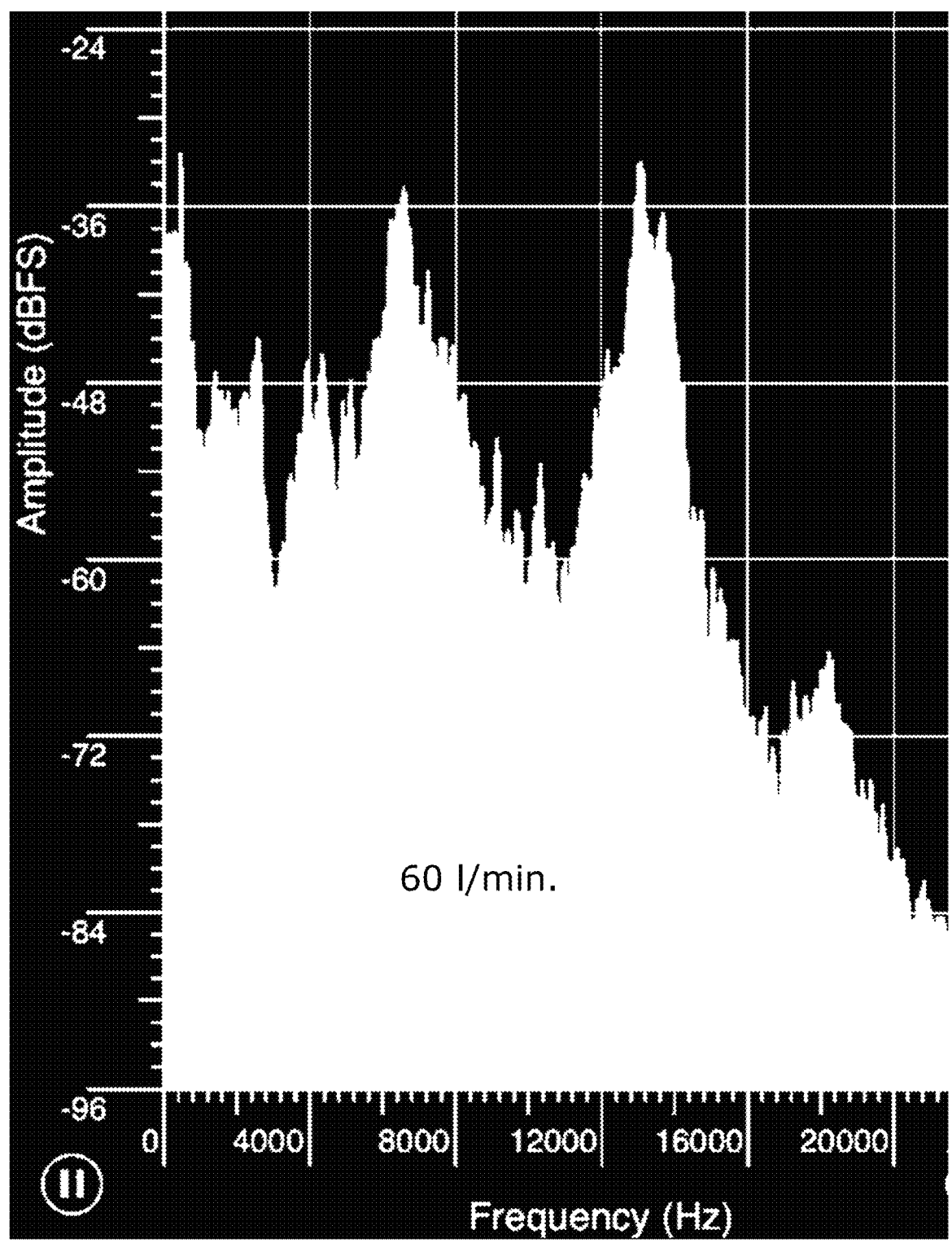
Figure 9D:
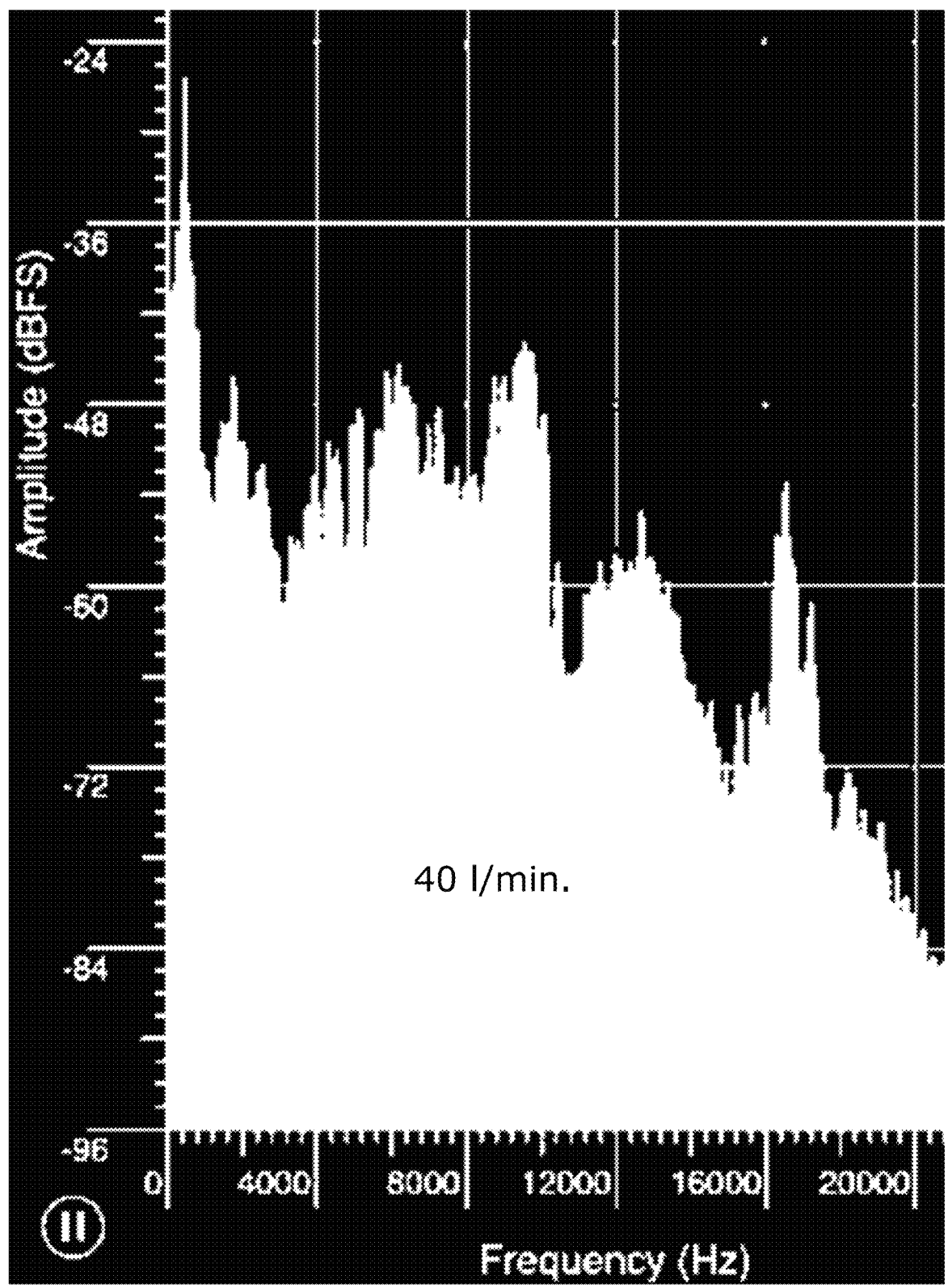

FIGS. 9c and 9d illustrate sound at an inhalation air flow speed of 60 l/min. and 40 l/min. for the embodiment of FIGS. 9a and 9b. Compared to FIGS. 8c and 8d, spectral peaks are seen at 60 l/min, but at lower frequency. Further, at lower flow speed 40 l/min., the shorter spacing between the gaps GP results in less distinct peaks compared with the inhaler embodiment of FIG. 8. In conclusion, the optimum distance between gaps GP should be selected according to individual targets.

Figure 10A:
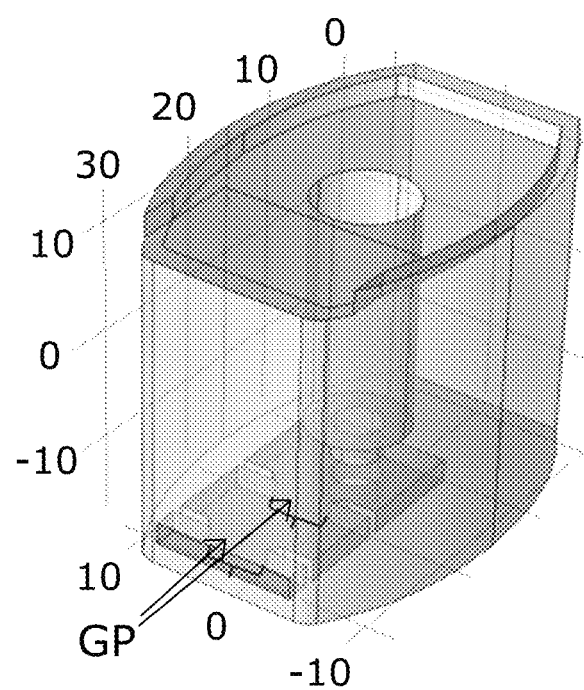
Figure 10B:
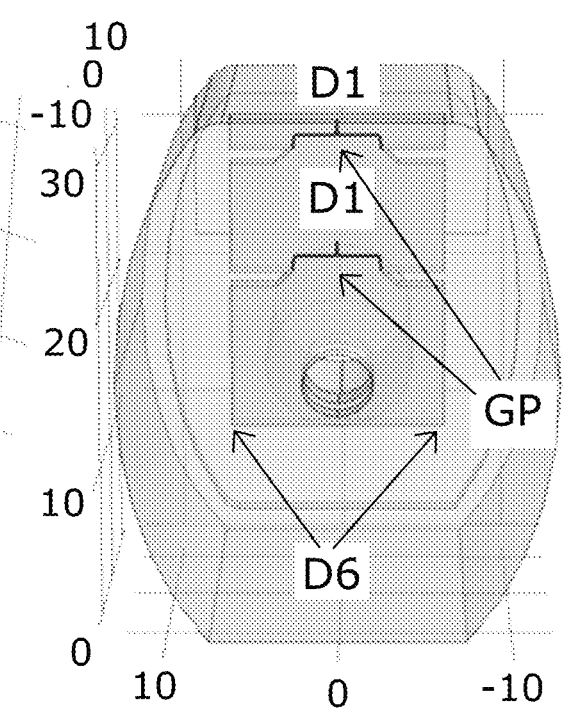

FIGS. 10a and 10b. show an inhaler similar to FIG. 8, but here with the passive acoustic element having the two gaps GP in series having shorter comb lengths (D4 referring to FIGS. 5a, 5b), namely such as 3 mm compared to about 5 mm in the previous examples. This is obtained compared to the previous embodiments, by the passive acoustic element having the same overall width D6, but with a larger gap distance D1 between each set of teeth than in the previous embodiments.

Figure 10C:
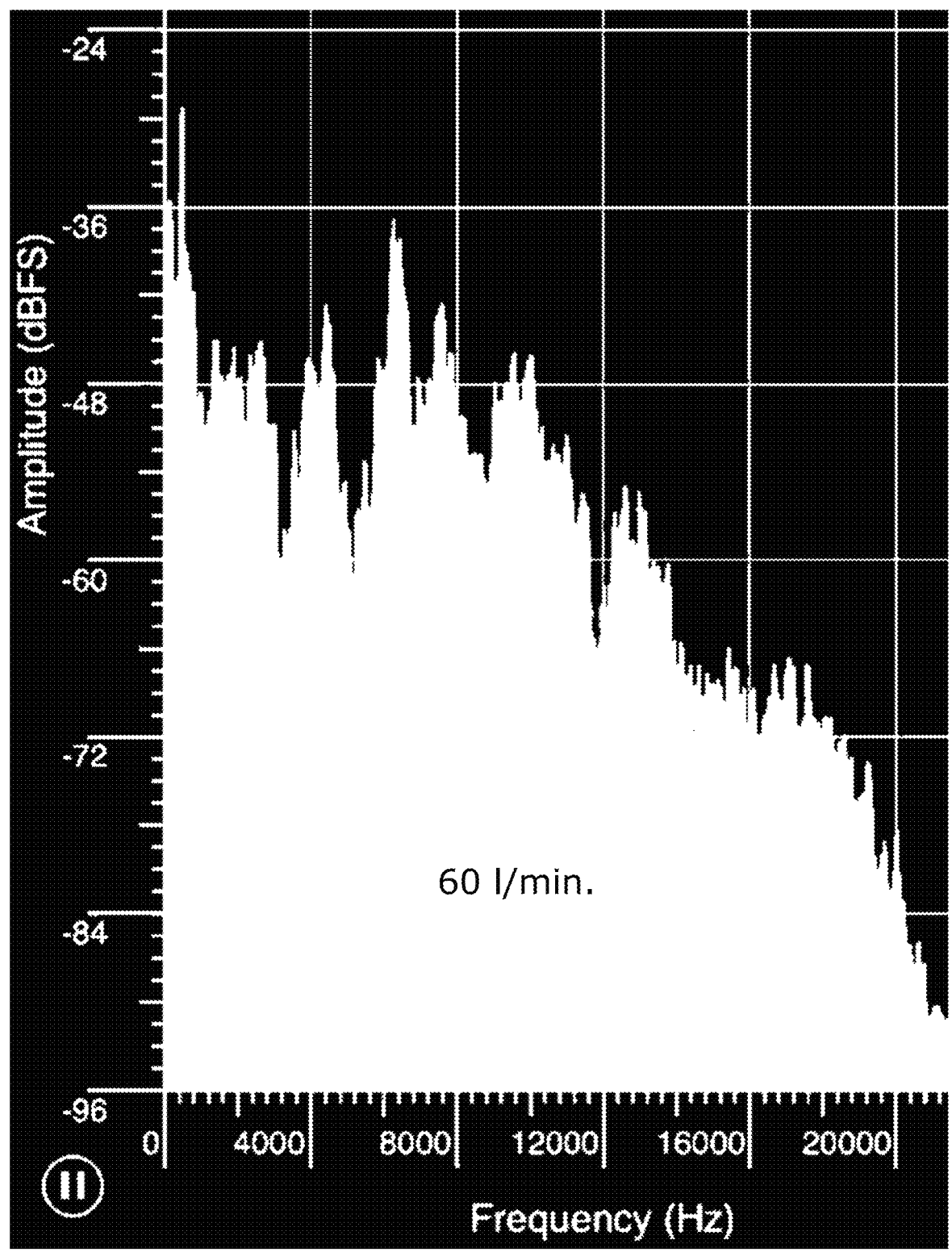
Figure 10D:
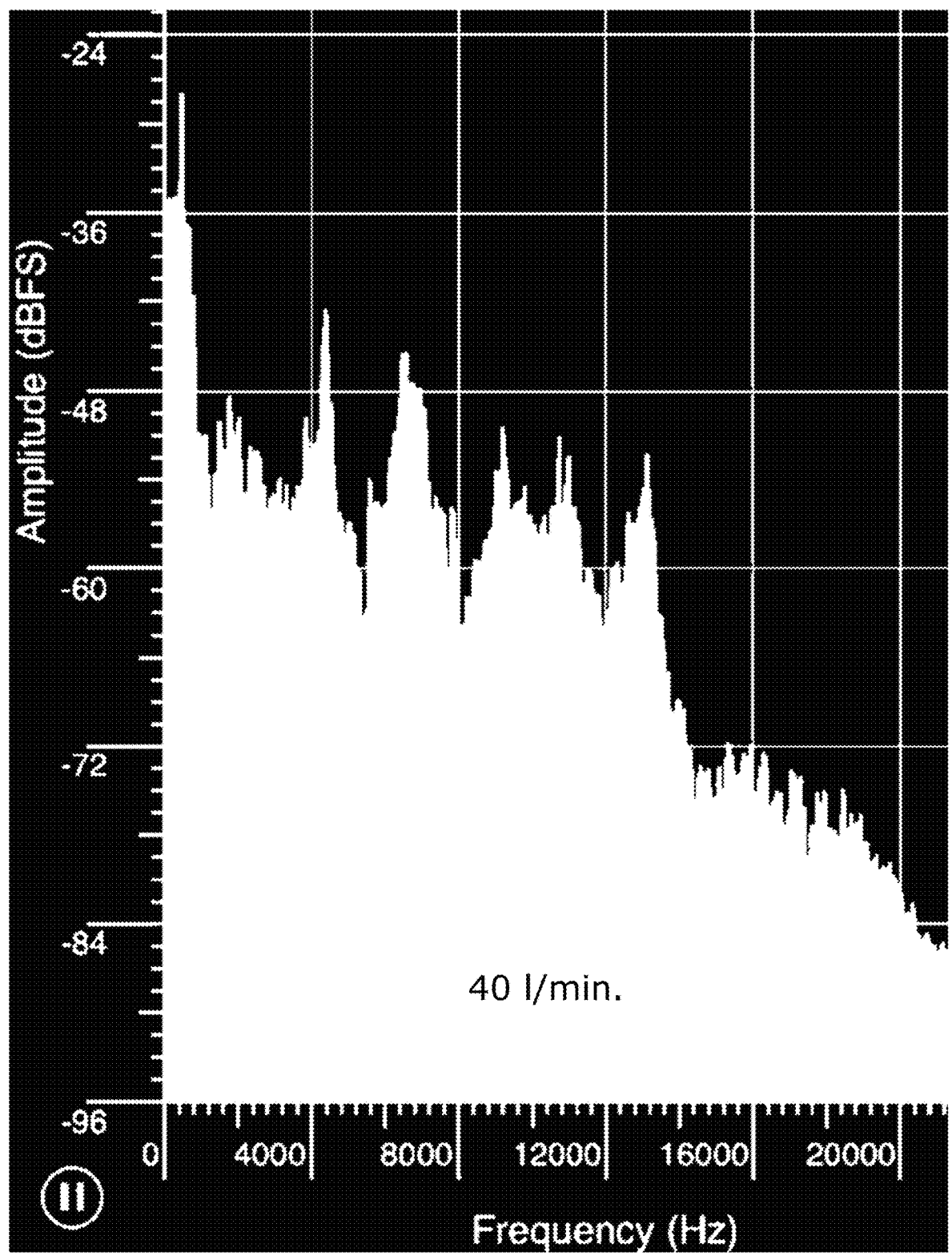

FIGS. 10c and 10d illustrate sound at an inhalation air flow speed of 60 l/min. and 40 l/min. for the embodiment of FIGS. 10a and 10b. As seen, compared to FIGS. 8c and 8d the spectral peaks can be observed, but they are less pronounced and distinct than in the embodiment of FIG. 8. Thus, an optimal gap length to achieve a desired sound has to be selected, e.g. depending on inhaler material, resolution (3D printing or other technologies) and the location of the passive acoustic element within the inhaler design.

To test the effect of 3D printing resolution on the resulting sound produced by the inhaler, the embodiment shown in FIG. 6 has been printed in two versions: one which is printed by a high resolution printer having a resolution of 60 µm (a high-end commercial 3D printer), and one which is printed by a low resolution printer having a resolution of 300 µm (such as Makerbot or Ultimaker 3D printer). The inhaler was tested without the mouth piece. Here, it was observed that the high resolution inhaler produced sound having a narrow peak with double the amplitude of the low resolution inhaler at a flow rate of 40 l/min. It is believed this is due to the higher printing resolution and hence more well defined and sharp edges of the gaps of the passive acoustic element. Thus, to produce the most distinct sound from the inhaler, which allows the most easy signal processing to correlate to air flow speed, it is preferred that a passive acoustic element with rather sharp edged on the gap(s) is used. In case of 3D printing, this appears to require a printing resolution better than 2-300 µm. Further, with a better manufacturing resolution, a more accurate geometry according to the selected design, e.g. length and width of the gap(s) (D4, D5 referring to FIGS. 5a, 5b).

Figure 11A:
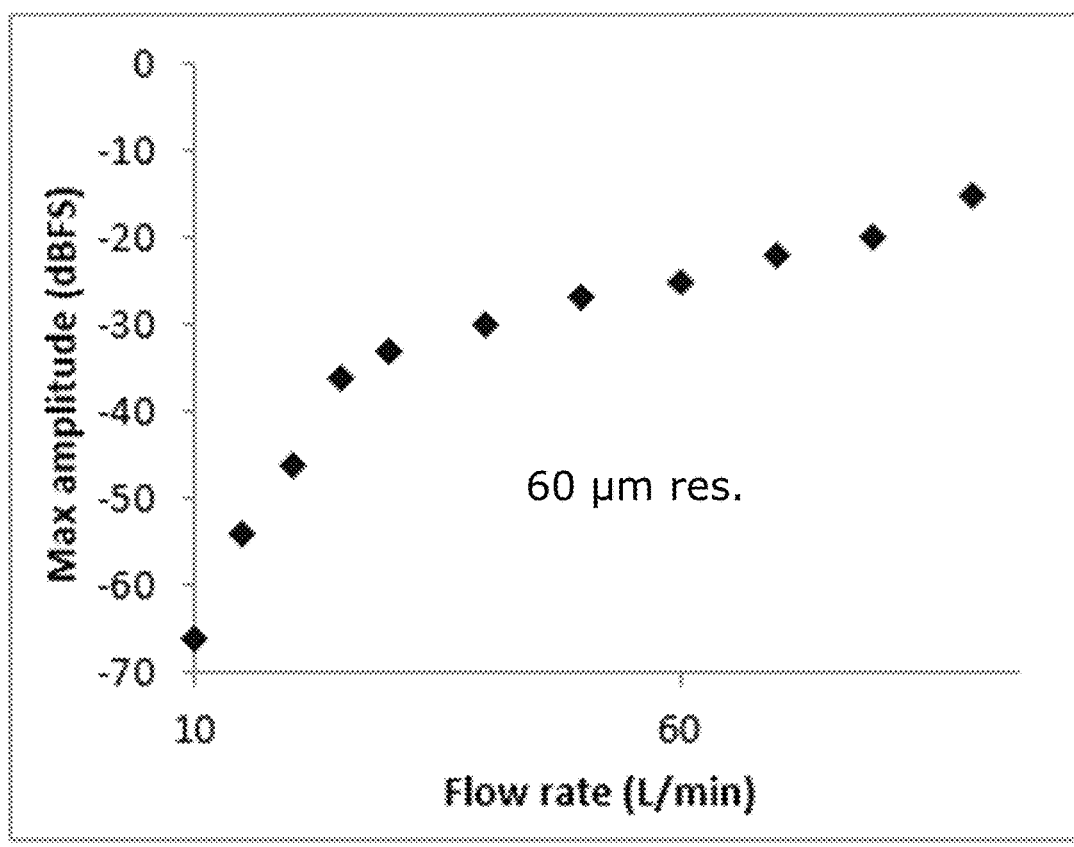
Figure 11B:
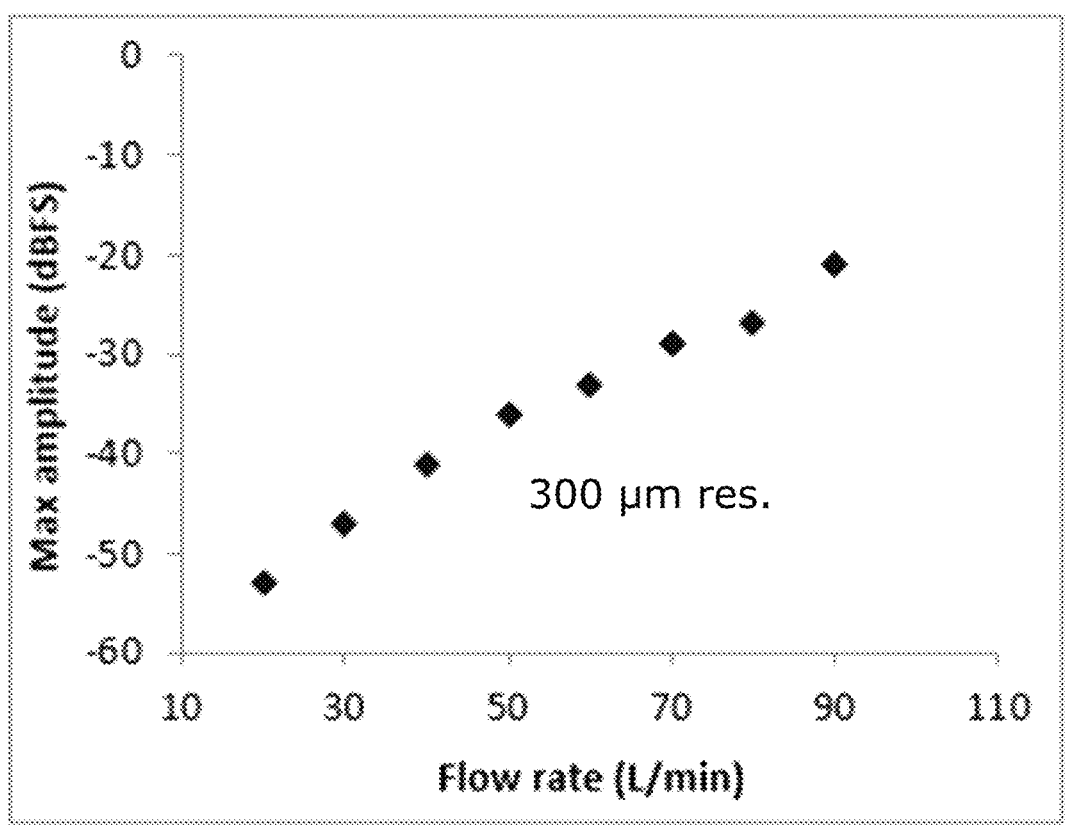

FIGS. 11a and 11b show graphs indicating sound amplitude versus air flow speed for the mentioned high resolution (60 µm) and low resolution (300 µm) inhaler versions. Both generally show increased sound amplitude with increasing air flow speed, but in general the sound amplitude produced by the high resolution inhaler is higher than the sound amplitude produced by the low resolution inhaler.

Figure 12A:
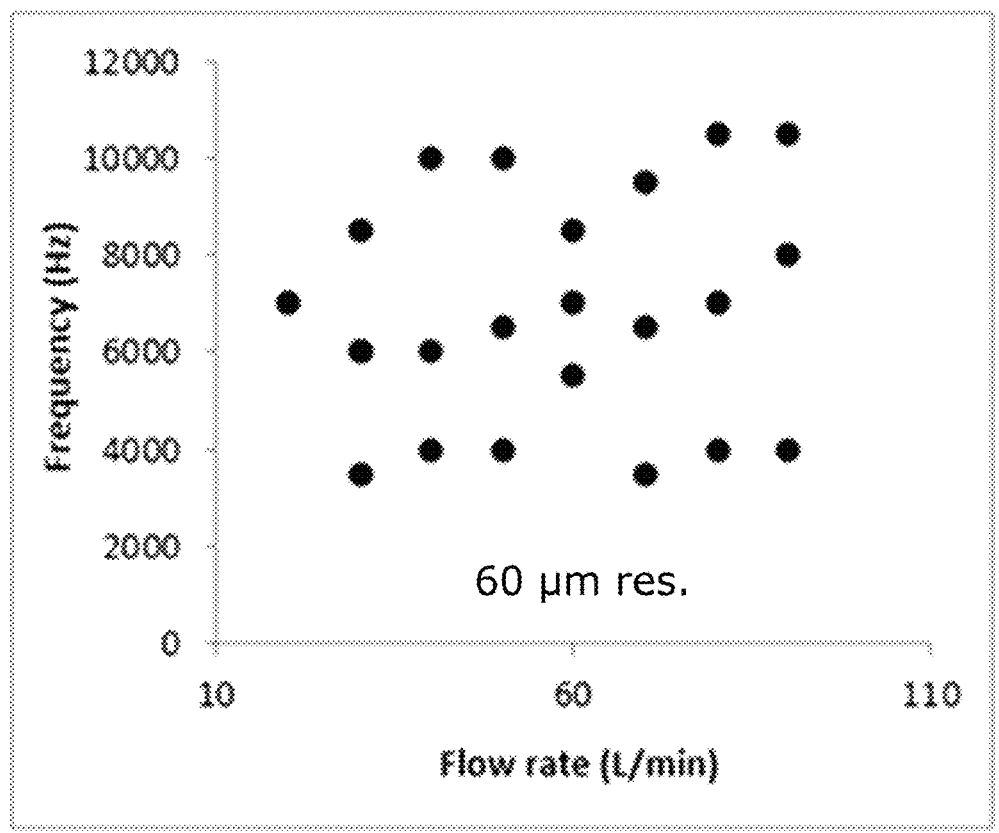
Figure 12B:
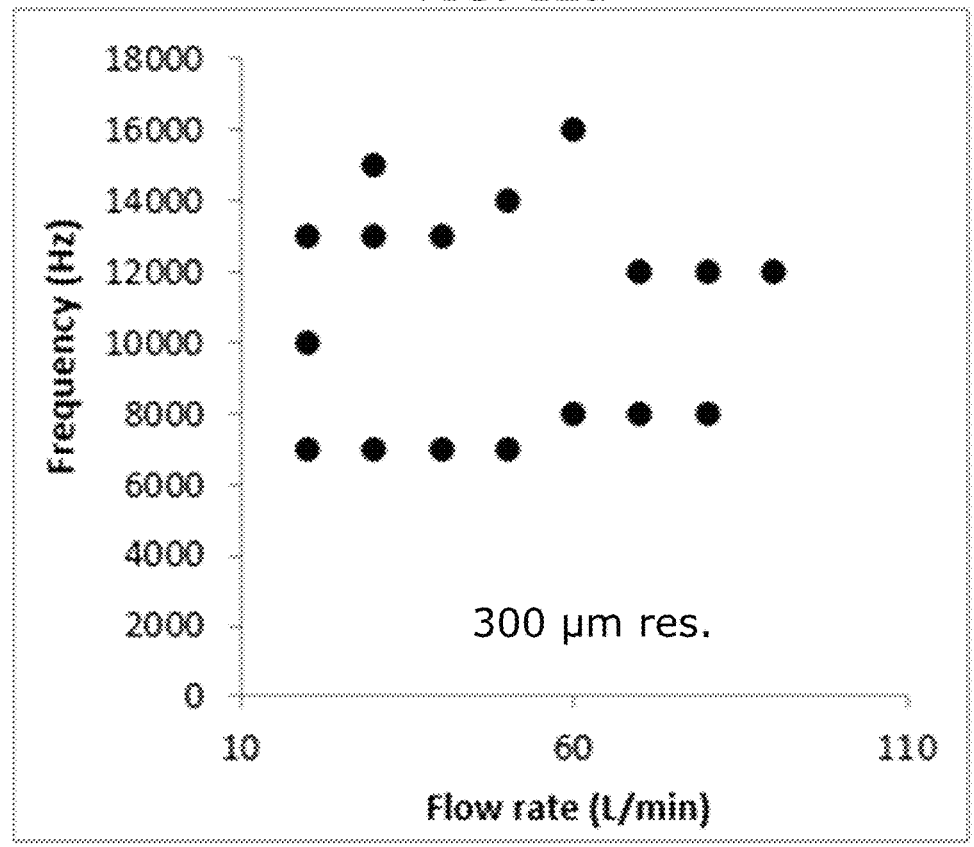

FIGS. 12a and 12b show graphs indicating spectral profile of sound versus air flow speed for the mentioned high resolution (60 µm) and low resolution (300 µm) inhaler versions. The two inhalers both show several peaks of different frequency for each flow rate, although a clear tendency in the frequencies as a function of flow rate was difficult to discern. It was observed that frequencies were generally higher for the low resolution version compared to the high resolution version.

A suitable processing algorithm, e.g. based on a training of a machine learning algorithm, can, regardless of possible chaotic air flow speed, be used to compute a measure of air flow speed based on the acoustic characteristics of the captured sound.

Figure 13A:
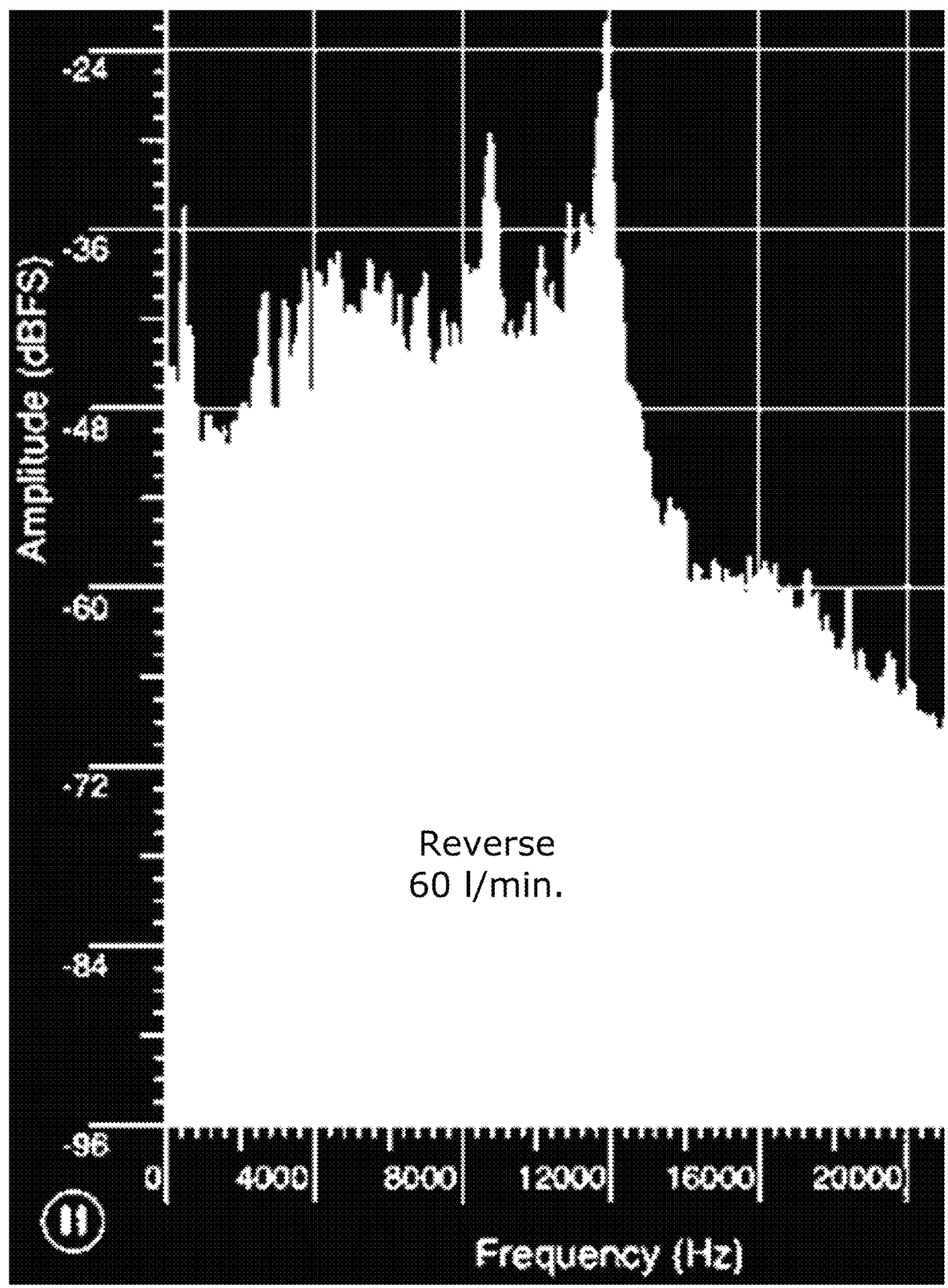
FIGS. 13a and 13b show sound spectra produced by exhalation through an inhaler embodiment.
Figure 13B:
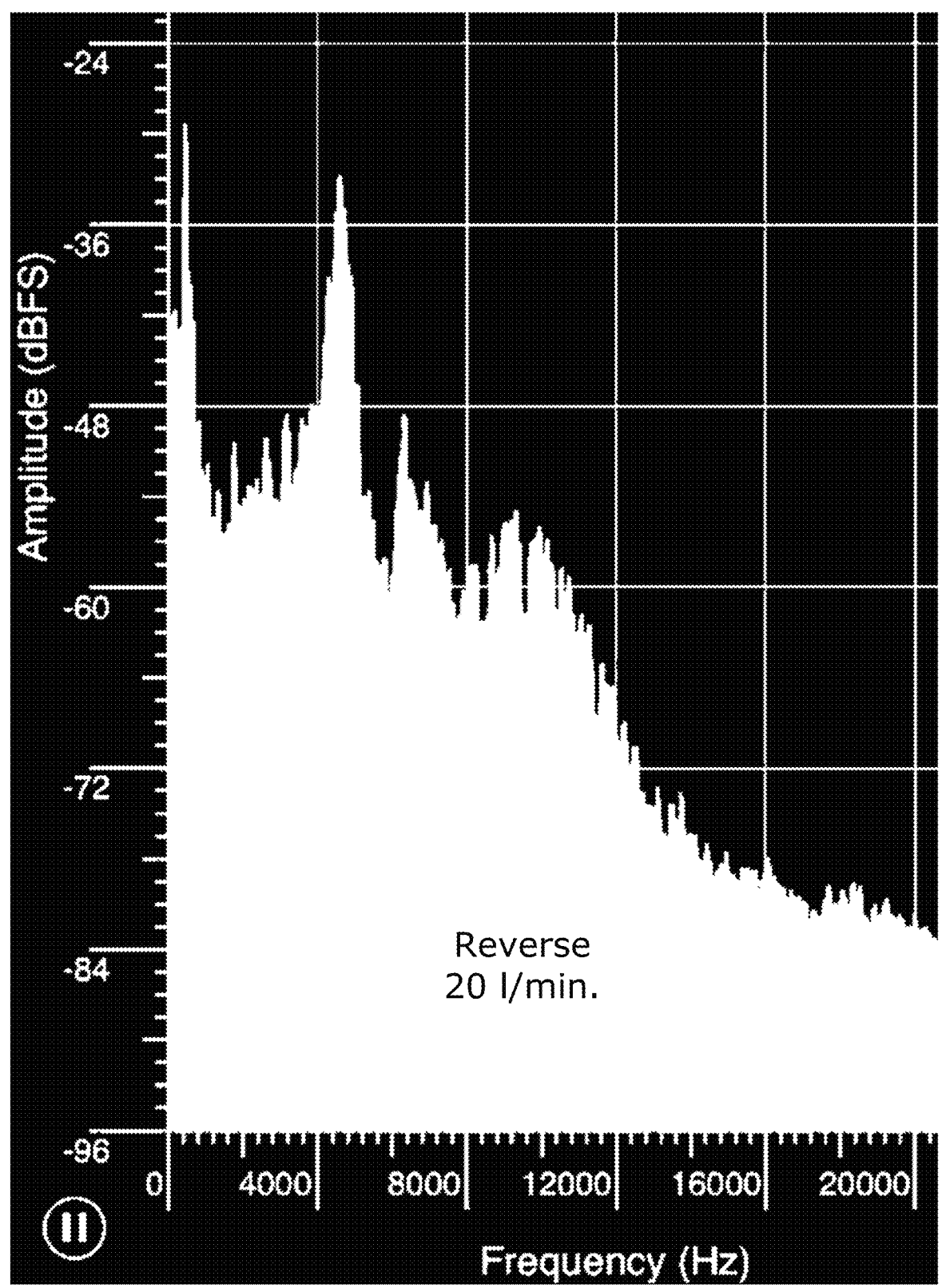

FIGS. 13a and 13b show spectra for sound produced by the effect of reversing the inhaler of FIG. 6, so as to test its function for exhaling into the inhaler. The high resolution version inhaler was used for this test, again without the mouth piece. As seen, a clear signal with distinctive peaks is observed both at an air flow speed of 60 l/min. and at 20 l/min. This demonstrated that the inhaler can also be used for exhalation, even though in the test, air was driven from the other end of the device. Blowing or exhaling air, however, shows similar results and can be performed from both ends of the inhaler.

The influence of adding a medicament capsule into the cavity of the inhaler housing was then assessed, again for the mentioned high resolution inhaler version. A commercial drug product with a capsule containing a drug dose intended for inhalation was placed in the inhaler and tested.

Figure 14A:
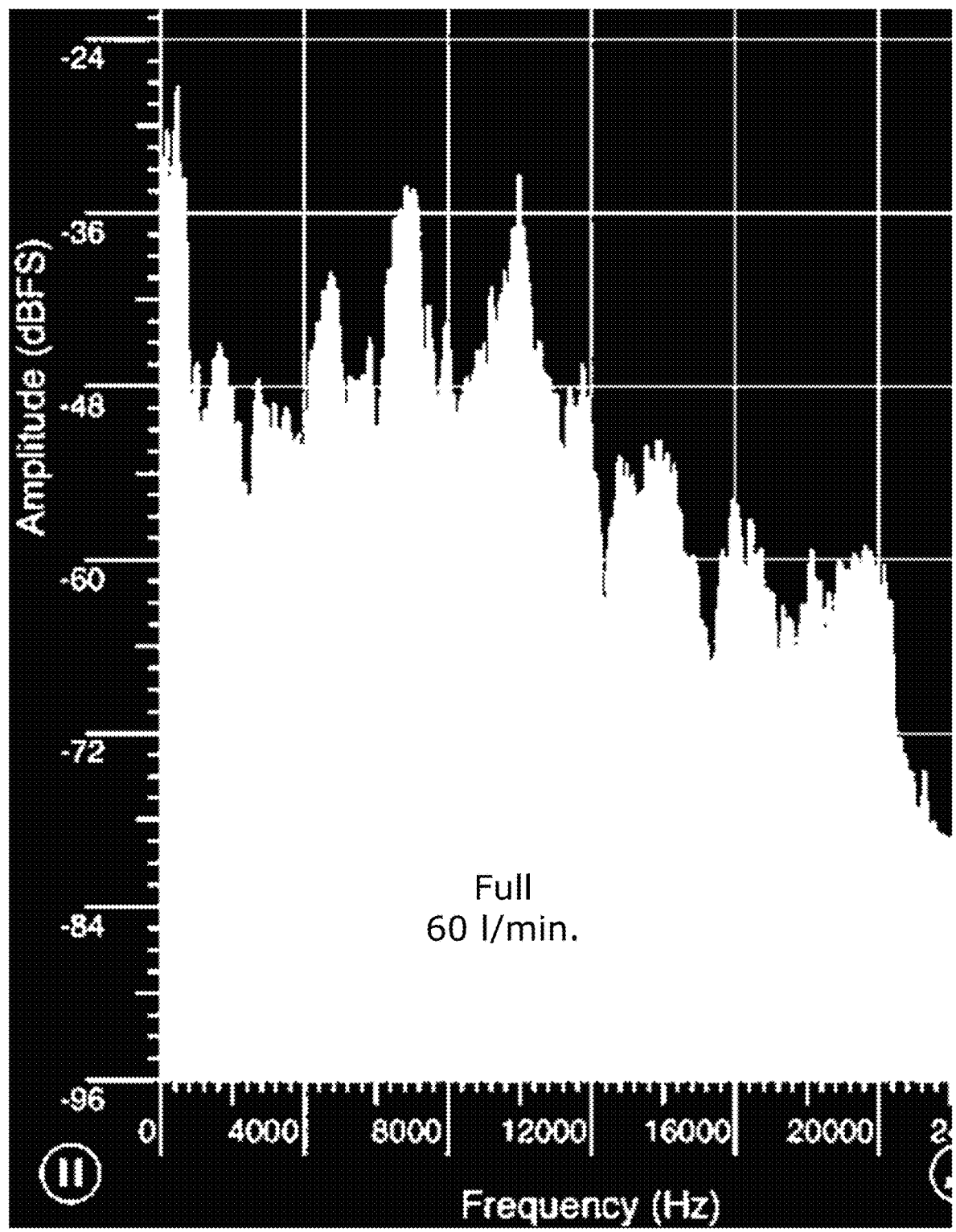
FIGS. 14a and 14b show sound spectra produced with a full and empty medicament capsule in the inhaler.
Figure 14B:
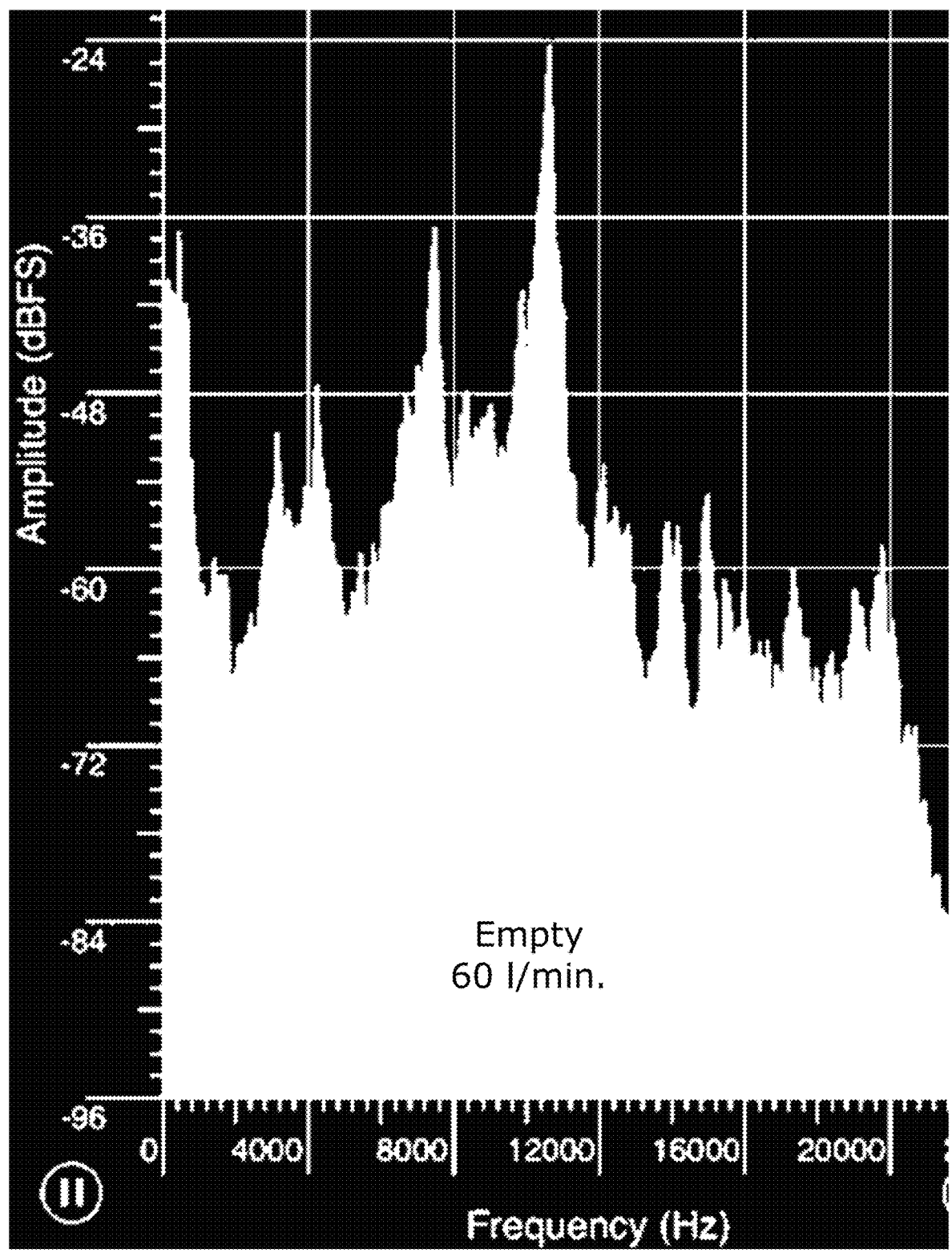

FIGS. 14a and 14b show sound spectra at 60 l/min. air flow speed for the full and empty medicament capsule. Inhalation using an unpierced capsule showed that the rotation of the capsule inside the inhaler results in significant fluctuations in the produced sound, and thus disrupts to a certain degree the spectral peaks otherwise observed. It can be observed from inspecting the sound signal as a function of time (not shown) that the sound fluctuates due to the rotational motion of the capsule. There are, however, still peaks that can be used for analysis of the air flow rate. The same trend was observed at different flow rates. With an empty capsule, the inhaler produces sound with much more distinct spectral peaks compared with the full capsule. The same profile was observed at different air flow speeds. For the empty capsule, fluctuations due to the rotation of the capsule were minor and did not have any influence on the captured sound. Although the capsule rotation sound may be considered as a disturbing effect on the sound from the inhalation, it can also provide information about the dosing of the medicament, including capsule emptying, and e.g. the rotational speed of the capsule may provide additional indications when analysed as a separate sound signal.

This demonstrates that it is easy to distinguish between a full and an empty capsule based on the sound captured or recorded from outside the inhaler. This is both due to differences in sound amplitude, and frequencies and the fluctuating patterns. This can thus be used to monitor correct administration of the dose using the inhaler and ensure that the patient is taking the required drug dose. The fluctuations in the signal can also be mitigated, if desired, by placing the passive acoustic element in a parallel flow path, e.g. as the inhaler embodiment in FIGS. 2a and 2b, where the same air does not pass over both the capsule chamber and passive acoustic element. It is possible that the sound from the rotating capsule can be captured by the sound capturer/recorder without influencing the sound produced by air flow passing the passive acoustic element. However, it may also be advantageous to make use of this fluctuating signal from the acoustic element, for monitoring purposes.

Figure 15A:
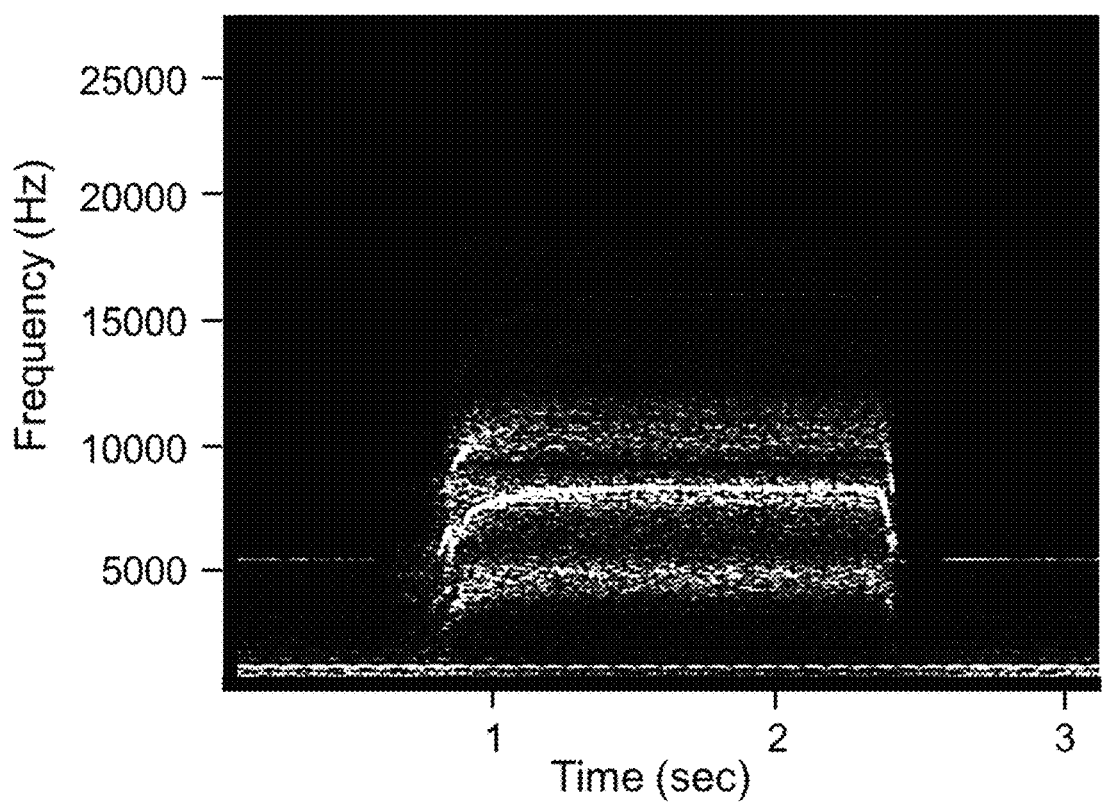
FIGS. 15a and 15b show sound spectra.
Figure 15B:
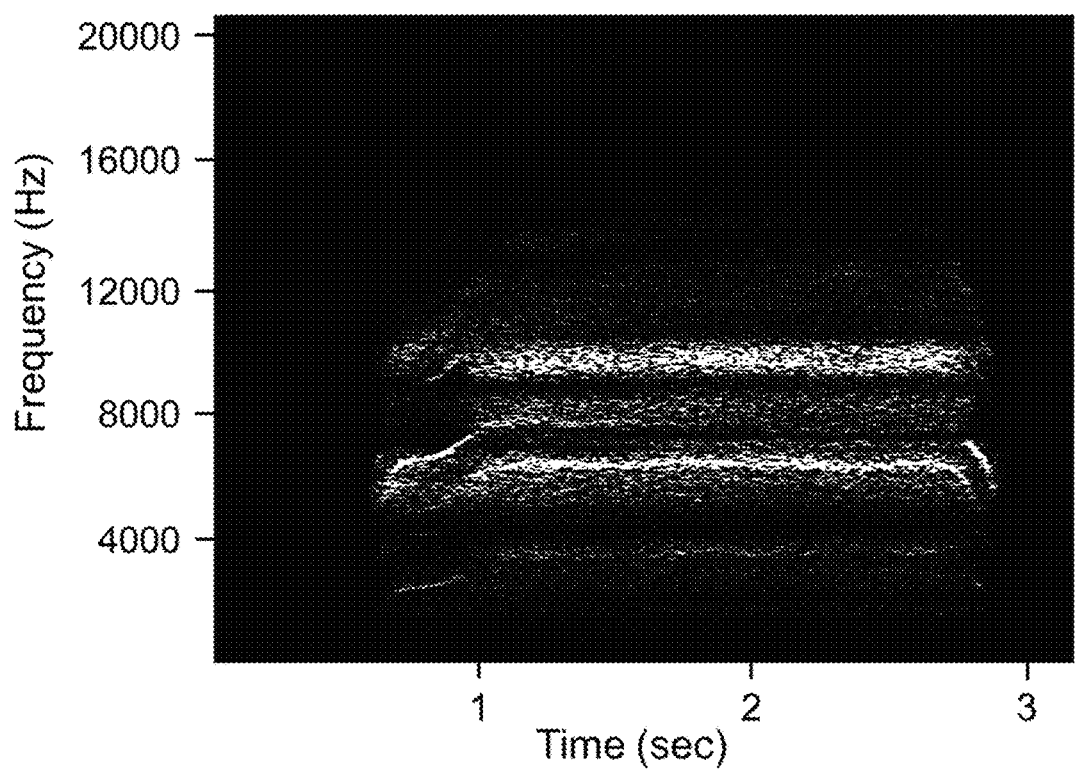

FIGS. 15a and 15b show graphs with examples of frequency analyses versus time profiles for sound generated by an inhaler produced with a high resolution (60 µm), i.e. indication of amplitude at various frequencies versus time. Black indicates low amplitude, and white indicates high amplitude. FIG. 15a shows the result for the inhaler exposed to a constant air flow of 60 l/min., while FIG. 15b shows the result for the same inhaler exposed to inhalation by a healthy male volunteer. FIGS. 15a and 15b illustrate the differences in signal over time observed when the acoustic inhaler is used. On one hand, the fixed flow rate using a vacuum pump (FIG. 15a) shows that a fixed flow rate can produce a fixed and constant sound while the acoustic element is exposed to the given pressure/flow. On the other hand, it also shows that an inhalation from a person can result in a more dynamic flow and sound profile, where the sound profile has more information that can be further processed and evaluated.

Figure 16:
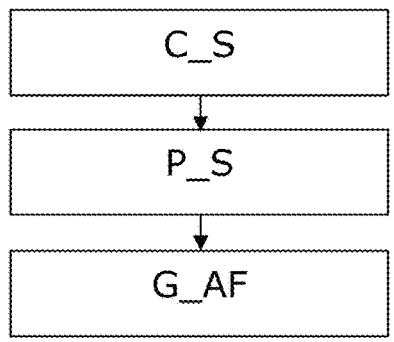
FIG. 16 illustrates steps of a method for measuring inhaled flow in an inhaler.

FIG. 16 shows steps of a method for measuring inhaled flow in an inhaler or inhaler add-on device according to the invention. The method comprises capturing sound C_S generated by the inhaler or inhaler add-on device during an inhalation. The sound is captured external to the housing, e.g. at a distance of such as 1 cm to 1 m, or 10 cm to 1 m, e.g. during a user inhaling a medicament through the air outlet of the inhaler. This can be done by the built-in microphone of a portable communication device, e.g. a smartphone. Next step is processing P_S the captured sound according to a processing algorithm. Finally the step of generating G_AF, a measure of inhaled air flow is performed, such as a measure of inhaled air volume and/or flow speed through the air outlet. In a more simple version, an output can be generated from the capturing device being such as a smartphone, indicating to the user and/or to another party, if a medicament dose has been inhaled through the air outlet or not.

Figure 17A:
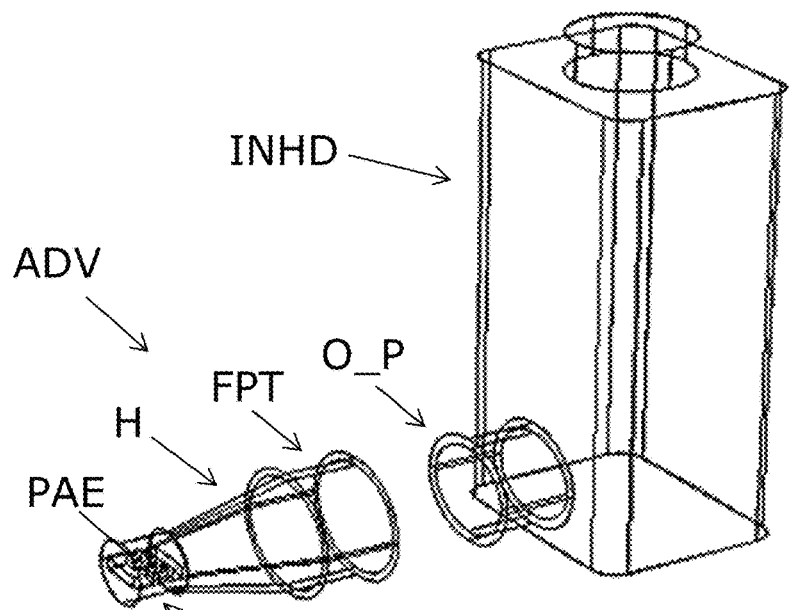
FIGS. 17a, 17b, and 17c show different views of an inhaler add-on embodiment.
Figure 17B:
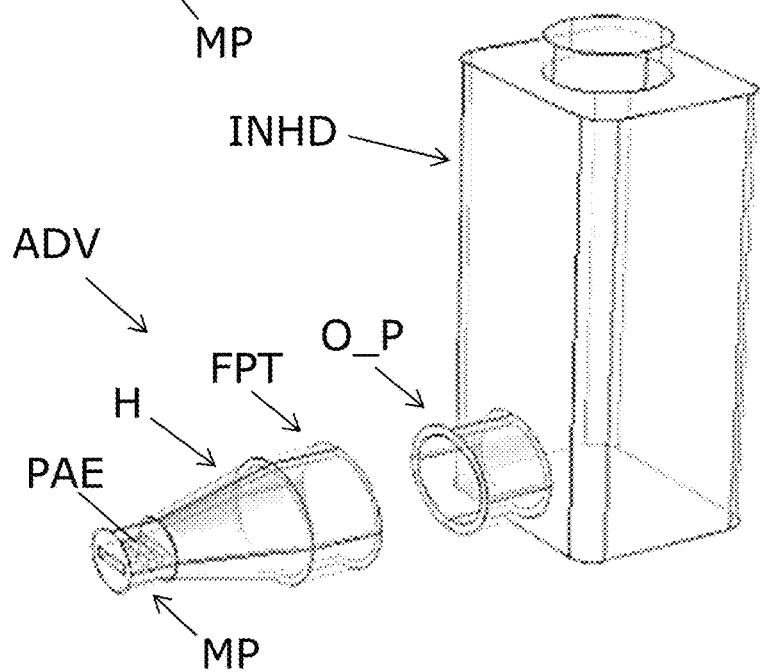
Figure 17C:
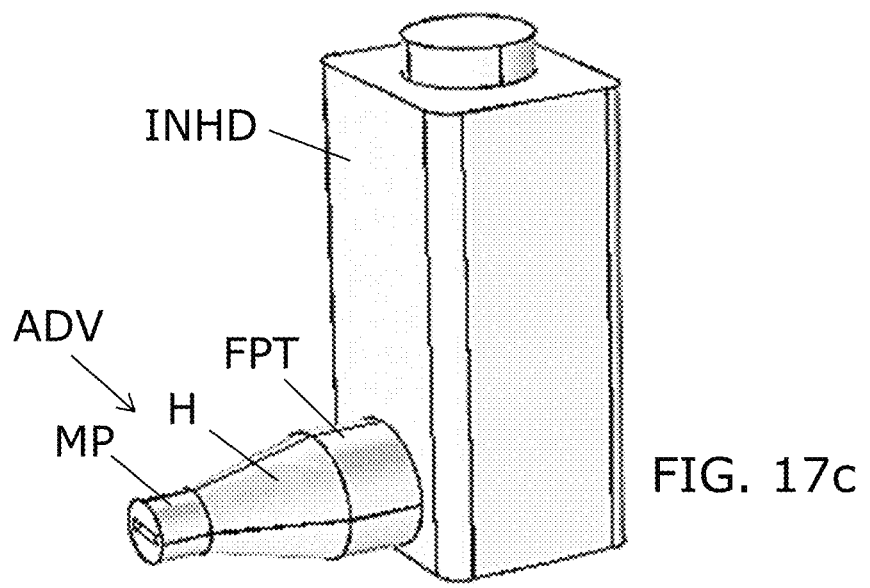

FIGS. 17a, 17b, and 17c show different views of an inhaler add-on embodiment ADV and an inhaler device INHD, e.g. a metered dose inhaler with an actuator on its top part for triggering an inhaled dose of medicament. Following the principles of the embodiments in the forgoing, the inhaler add-on device ADV has a housing H with a mouth piece MP in one end, and a fitting part FPT at the opposite end. The mouth piece MP is arranged for contact with the user's mouth during inhalation, and the fitting part FPT is arranged for connection to the inhaler INHD by attachment of the fitting part FPT to an air outlet pipe O_P of the inhaler INHD, so as to lock the add-on device ADV in position relative to the inhaler INHD for use.

As seen, the fitting part FPT is shaped so as to receive the air outlet pipe O_P of the inhaler and to allow locking of the position of the inhaler add-on device to the inhaler upon insertion of the outlet pipe of the inhaler into the fitting part FP of the inhaler add-on device ADV. The mouth piece MP has an outer circular or elliptical cross sectional area which is smaller than an outer cross sectional area of the fitting part FPT, and the same applies to inner cross sectional areas, i.e. the part of the housing H constituting the flow path between inhaler INHD and mouth piece MP. The size of the mouth piece MP can be dimensioned so as to fit the user, and it is not in any way limited by the dimensions of the acoustic element PAE.

The fitting part FP is preferably shaped to fit to the shaped and dimensions of the outlet pipe O_P of the inhaler INHD, so as to allow the user to simply press the add-on device ADV onto the outlet pipe O_P to lock its position for use. The user can either leave the add-on device ADV on the inhaler INHD for the next use, or take off the add-on device ADV e.g. for replacement, such as the add-on device ADV being a disposable. Alternatively, the inhaler INHD is a single-use device, while the add-on device ADV can be used multiple times. E.g. both the inhaler and the add-on may be used multiple times and for instance used for the same time span, e.g. 30 doses inhaled over 30 days etc. The add-on device can also be taken off and cleaned if needed, and it can be washed and cleaned which may be possible especially in cases where the add-on device if formed by a monolithic polymeric element.

The add-on device can also be taken off and cleaned if needed. It can in theory be washed and cleaned as it most likely only consists of a plastic monolith The passive acoustic element PAE is arranged inside the mouth piece MP and with one opening connected to the opening of the mouthpiece MP and the opposite opening connected to a flow path inside the housing H. This means that the medicinal dose will pass through the passive acoustic element PAE in this case. Depending on the medication taken this could provide a subtle but distinct and different sound signal when the medicinal dose goes through the passive acoustic element PAE. The housing H is shaped to provide a straight flow path between the mouth piece MP and the fitting part FP. Of course, depending on the design of the inhaler INHD to fit with the add-on device, the flow path between fitting part FP and mouth piece MP may be bend or curved.

Figure 18A:
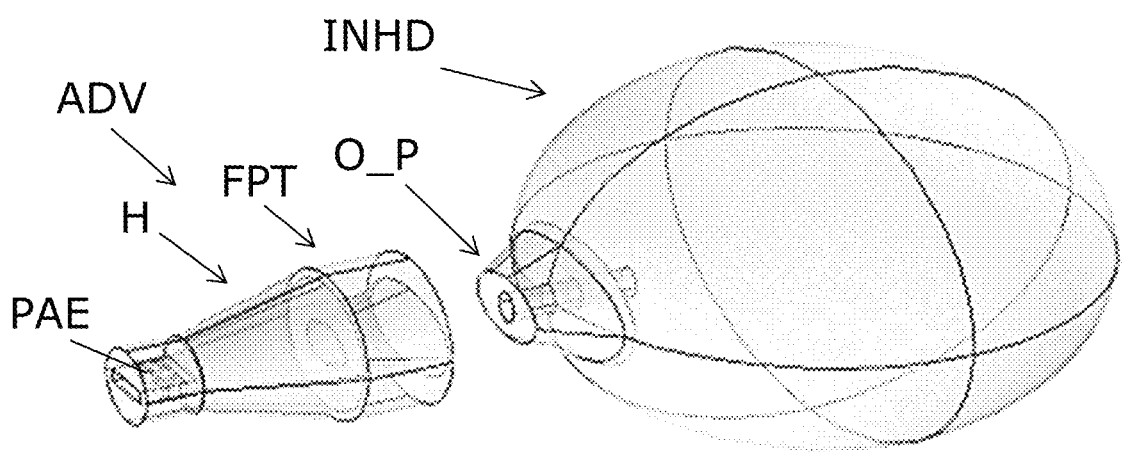
FIGS. 18a and 18b show different views of another inhaler add-on embodiment.
Figure 18B:
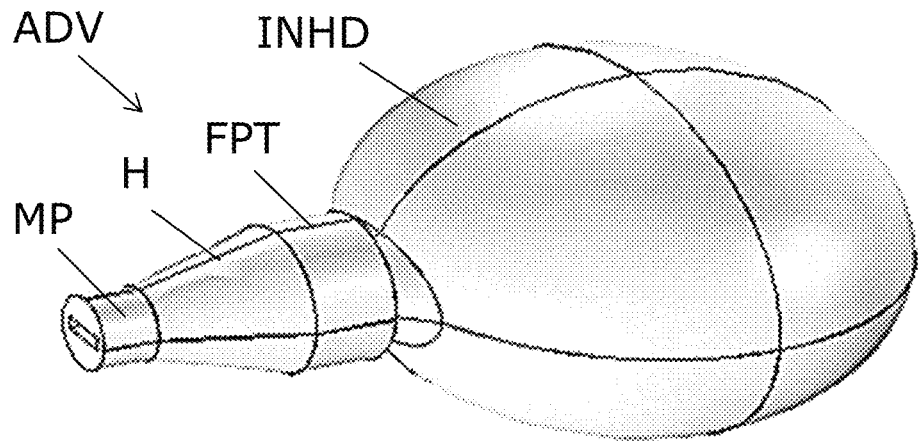

FIGS. 18a and 18b show another inhaler add-on embodiment similar to the one in FIGS. 17a-17c, but shaped to fit to another type of inhaler INHD, here a dry powder type inhaler without an actuator, thus having a differently shaped fitting part FPT arranged to shape the outlet pipe O_P of this inhaler INDH.

Figure 19A:
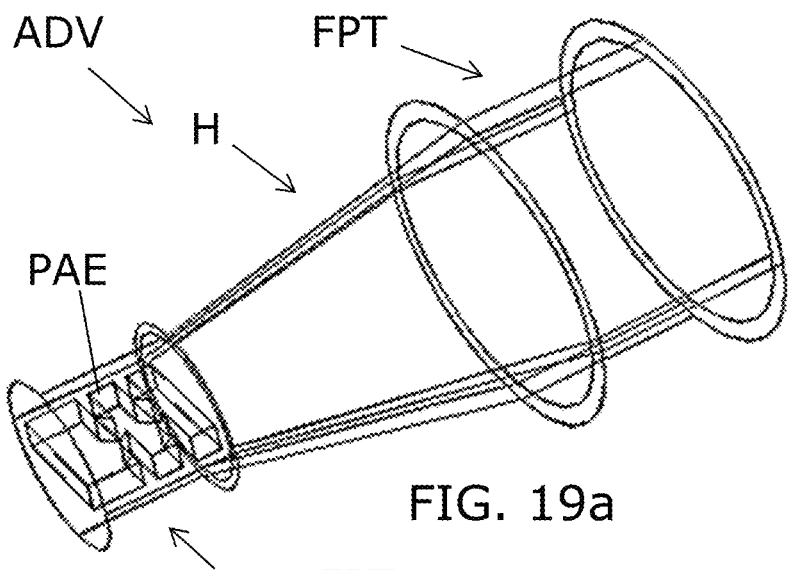
FIGS. 19a, 19b, and 19c show different views of the add-on embodiment of FIG. 17,
  FIGS. 20a, 20b, and 20c show different views of an inhaler add-on embodiment with a housing branch where the passive acoustic element is positioned.
Figure 19B:
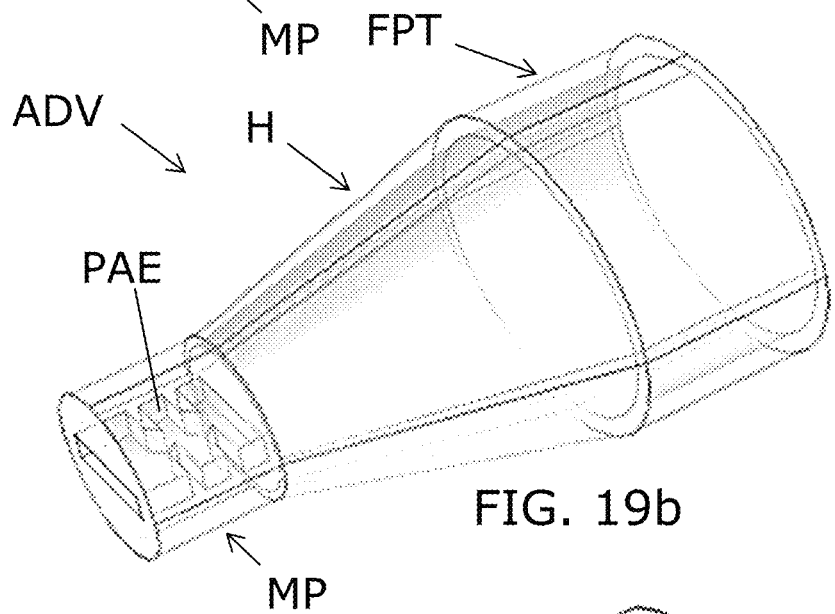
Figure 19C:
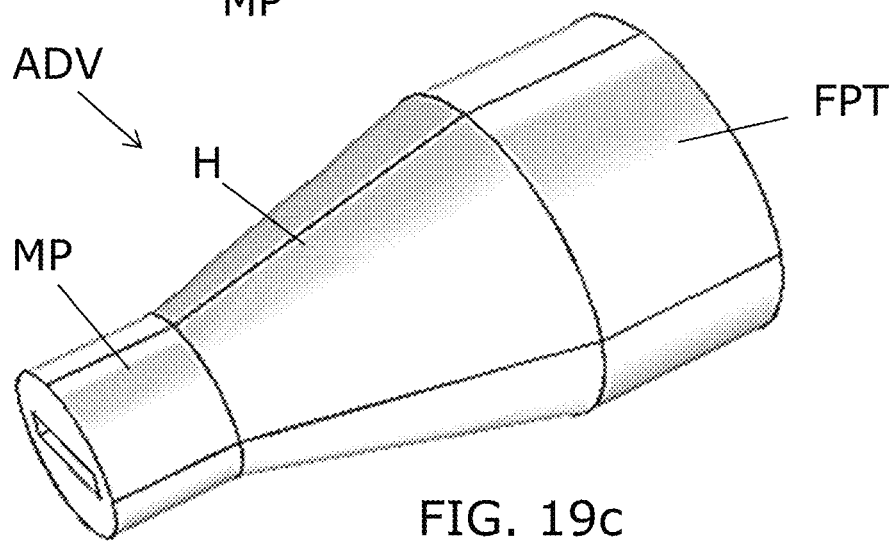

FIGS. 19a, 19b, and 19c show larger views of the add-on embodiment of FIG. 17. Here, the specific passive acoustic element PAE in the mouth piece MP with two gaps is shown. It is to be understood that the passive acoustic element PAE can be designed differently, as already described in previous embodiments.

Figure 20A:
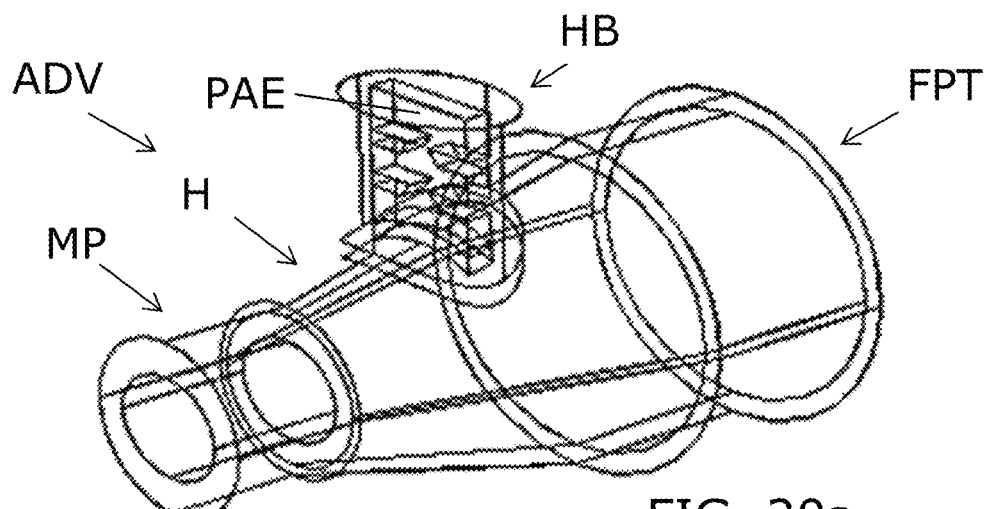
Figure 20B:
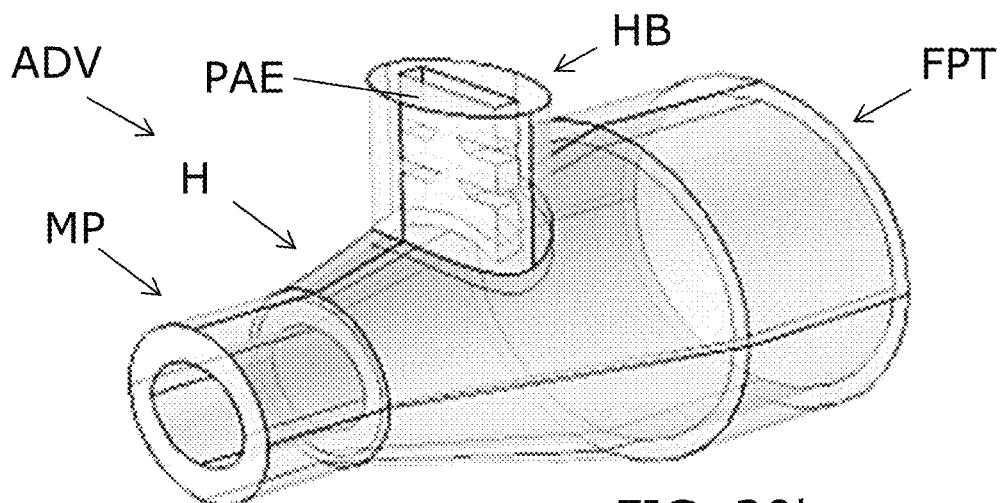
Figure 20C:
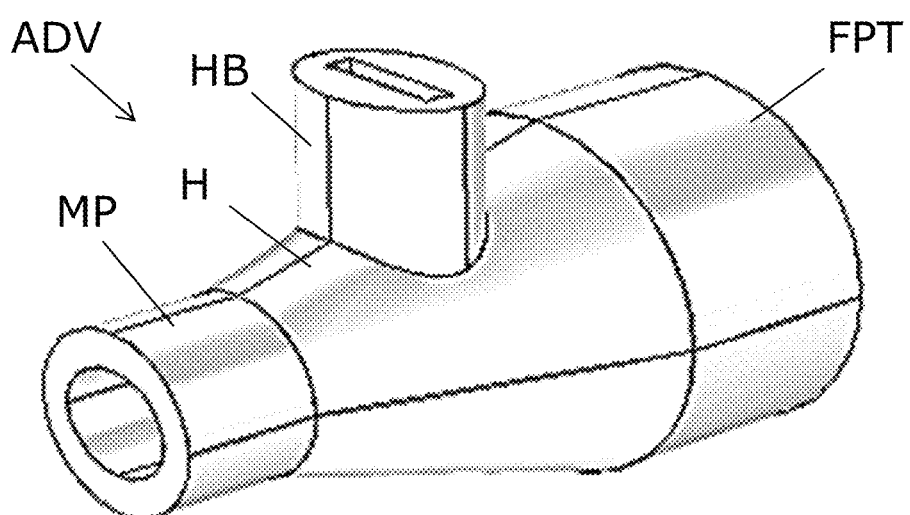

FIGS. 20a, 20b, and 20c show different views of an inhaler add-on embodiment ADV which is similar to the one in FIGS. 19a-19c, except that the passive acoustic element PAE is here placed in a housing branch HB, and not in the mouth piece MP. The housing branch HB is designed to provide only limited part of an air flow through the mouth piece, such as 5-50%, e.g. 5-15%, of an air flow through the mouth piece MP, which may be advantageous to avoid high air flows and e.g. disturbance of medicaments from the inhaler.

As seen, the passive acoustic element PAE is arranged in an air flow path between an opening of the housing branch HB and air flow inside the housing H, i.e. the housing branch has an opening to the environment which is separate from the the openings in the mouth piece MP and the opening in the fitting part FP. As seen, in this embodiment, the housing branch HB is designed so that the passive acoustic element PAE is arranged in a flow path with a flow direction being perpendicular to the main flow path direction in the mouth piece MP, and the flow direction between the fitting part FP and the mouth piece MP.

Figure 21A:
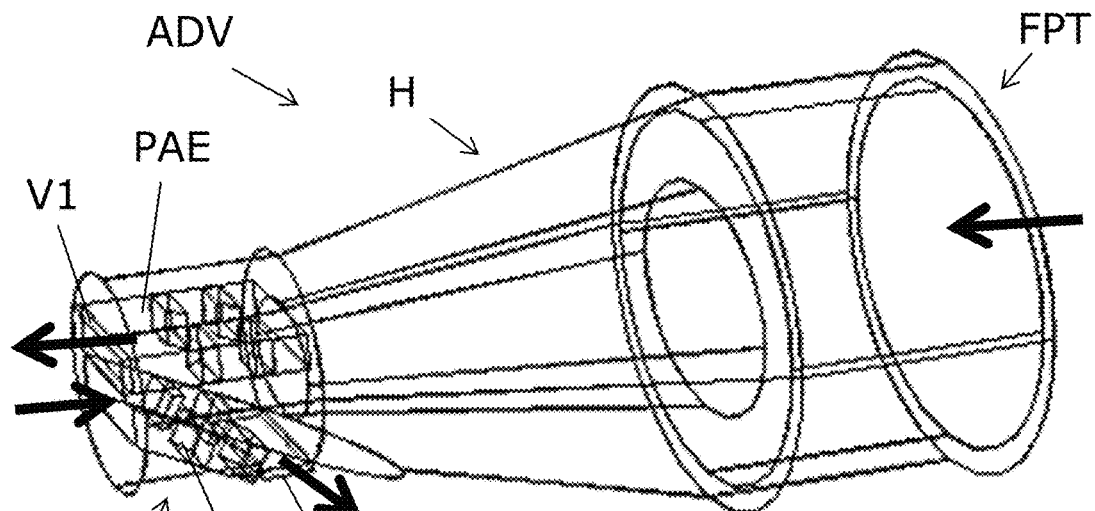
FIGS. 21a, 21b, and 21c show different views of an inhaler add-on embodiment for both inhalation and exhalation, and with two separate passive acoustic elements.
Figure 21B:
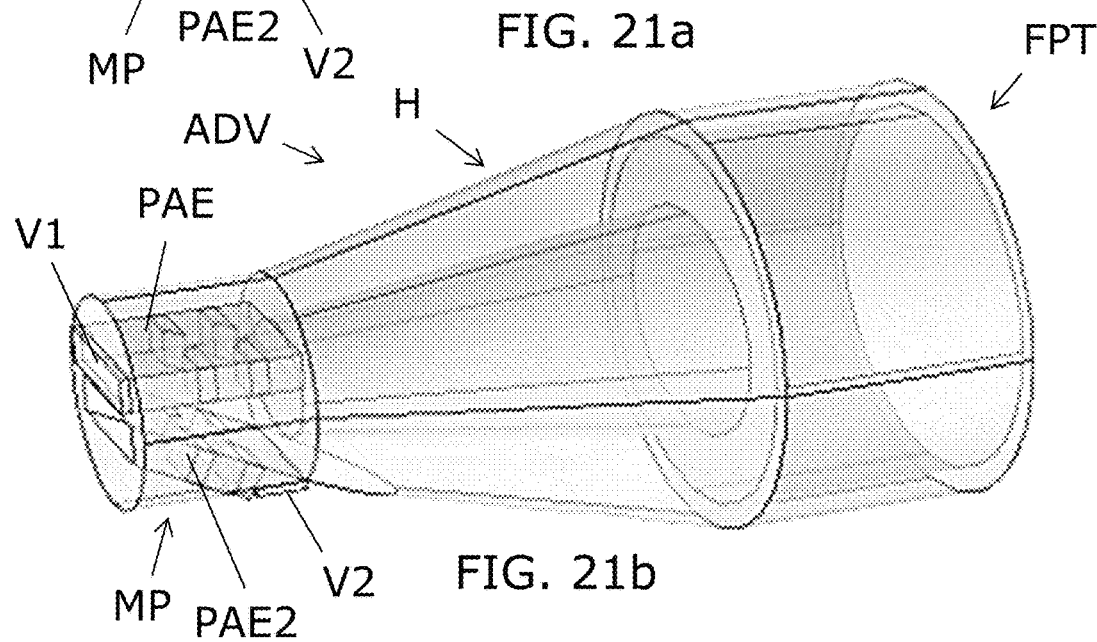
Figure 21C:
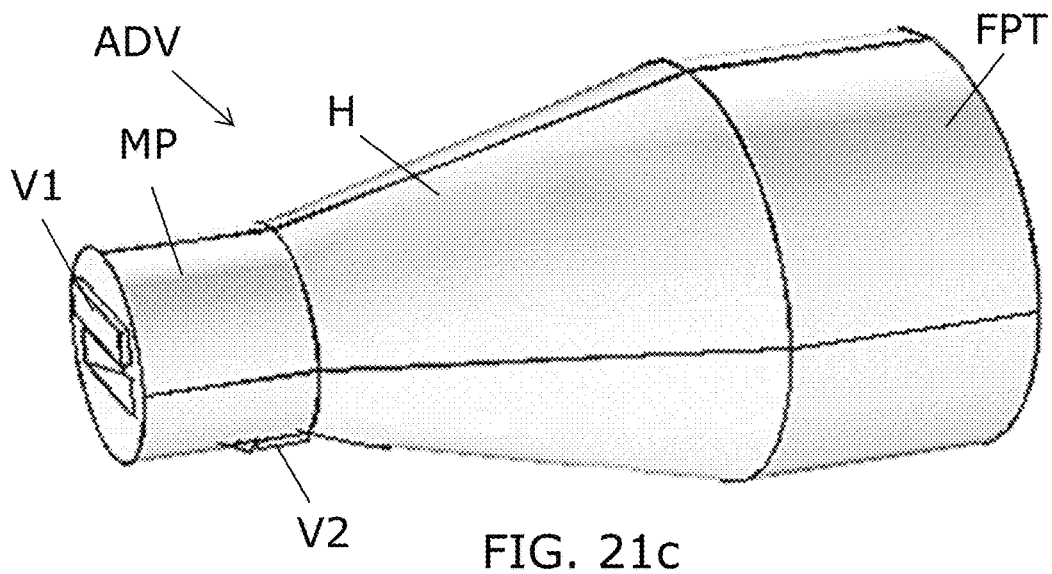

FIGS. 21a, 21b, and 21c show different views of an inhaler add-on embodiment ADV similar to the one in FIG. 19, but here the mouth piece MP is arranged to receive exhaled air, so as to allow acoustic monitoring of exhaled air flow external to the add-on device upon a user exhaling air into the mouth piece MP. Thus, in this embodiment ADV, acoustic monitoring of both inhalation and exhalation is possible.

Two separate passive acoustic elements PAE, PAE2 are used, one PAE for inhalation and one PAE2 for exhalation by means of a first valve V1 arranged to block exhaled air flow from passing the first passive acoustic element PAE, and a second valve V2 arranged to block inhaled air flow from passing the second passive acoustic element PAE2. Bold arrows indicate inhalation and exhalation flow directions through the device ADV. For exhalation, the second passive acoustic element PAE2 is connected to receive air flow in the mouth piece opening, while the opposite end is connected to an opening of the housing H_where the second valve V2 is positioned to block incoming air during inhalation through the mouth piece MP.

As seen, both passive acoustic elements PAE, PAE2 are arranged inside the mouth piece MP part of the housing H, and these two elements may be different or identical. Other positions of the passive acoustic elements PAE, PAE2 may be chosen, e.g. a combination of the ones shown in embodiments in FIGS. 19 and 20.

In general, outer shape and dimensions of an inhaler add-on device should be fitted to an actual inhaler type, shape and dimension.

In the following, inhaler embodiments of the invention will be defined as E1-E10.

E1. An inhaler for dispensing a medicament to be inhaled, the inhaler comprising
    a housing (H) comprising an air inlet (A_I), and an air outlet (A_O), such as comprising a mouthpiece (MP) for outputting air to be inhaled by a user, wherein the housing (H) defines a flow path (FP) between the air inlet (A_I) and air outlet (A_O), and
    a first passive acoustic element (PAE) arranged in the flow path (FP) inside the housing (H) and dimensioned such that air flow passing the first passive acoustic element (PAE) will generate sound (S) with pre-determined characteristics depending on flow speed of air passing the first passive acoustic element (PAE), so as to allow acoustic monitoring of air flow passing the first passive acoustic element (PAE) external to the housing (H),
    wherein the first passive acoustic element (PAE) comprises a structure having one or more gaps arranged to be passed by an air flow.

E2. Inhaler according to E1, wherein the one or more gaps are shaped and separated by a distance (D2) so as to generate sound depending on air flow speed with pre-determined characteristics comprising at least one of: amplitude, and spectral components.

E3. Inhaler according to E2, wherein the one or more gaps are shaped and separated by a distance (D2) so as to generate sound (S) depending on flow speed with pre-determined characteristics comprising at least one spectral peak, preferably 2-4 spectral peaks.

E4. Inhaler according to any of E1-E3, wherein said one or more gaps are straight gaps which are perpendicular or substantially perpendicular to a direction of air flow passing the first passive acoustic element (PAE).

E5. Inhaler according to any of E1-E4, wherein the first passive acoustic element (PAE) comprises a structure having teeth defining one or more gaps (GP) between them, wherein the one or more gaps (GP) being a passage through the structure with no material being present in the gap (GP).

E6. Inhaler according to any of E1-E5, wherein the first passive acoustic element (PAE) is positioned in the flow path (FP) downstream of an inhaler medicament compartment (MC) for providing medicament to be inhaled.

E7. Inhaler according to any of E1-E6, wherein the air inlet (A_I) or air outlet (A_O) of the housing (H) is arranged for connection to a separate device, wherein said separate device comprises a compartment comprising a medicament to be inhaled.

E8. Inhaler according to E1-E7, further being arranged to receive exhaled air via the air inlet (A_I) or the air outlet (A_O), so as to generate sound with pre-determined characteristics depending on flow speed of air passing the first passive acoustic element (PAE), so as to allow acoustic monitoring of air flow passing the first passive acoustic element (PAE) external to the housing (H) upon a user exhaling air into the air inlet (A_I) or air outlet (A_O).

E9. Inhaler according to E1-E9, wherein the first passive acoustic element (PAE) is formed as a monolithic part of the housing H.

E10. A system comprising an inhaler according to any of E1-E9, and
    a device (SP), such as a smart phone, arranged to capture sound (S) generated by the inhaler during an inhalation, wherein the device comprises a processor (P) arranged to process the captured sound (S) according to a processing algorithm and to generate a measure of air flow through the air outlet (A_O) of the inhaler in response to the processing algorithm, preferably so as to determine if a dose of medicament has been inhaled.

Such inhaler device and system as in embodiments E1-E10 is advantageous, since it has been proven to be possible to provide an inhaler with a very simple structure, including the passive acoustic element with structured gaps, which allows e.g. 3D printing of the entire inhaler. This allows the inhaler to be manufactured as a disposable product and/or to be produced at the point of need, e.g. by the user or at a hospital etc. The inhaler does not require any electrical components inside or on the housing, since the sound is generated by a passive acoustic element, in the same manner as a whistle.

To sum up, the invention provides an inhaler or an add-on device for an inhaler for dispensing a medicament to be inhaled. The inhaler or add-on device has a housing H with an air inlet A_I, and an air outlet A_O for outputting air to be inhaled by a user. The housing H defines a flow path FP between the air inlet A_I and air outlet A_O, and a passive acoustic element PAE is arranged in this flow path FP inside the housing H. The passive acoustic element PAE has a structure having one or more gaps arranged to be passed by an air flow and it is dimensioned such that air flow passing it will generate sound S with pre-determined characteristics depending on the air flow speed. This allows acoustic monitoring of air flow passing the first passive acoustic element PAE external to the housing H by capturing and processing sound generated.

Although the present invention has been described in connection with the specified embodiments, it should not be construed as being in any way limited to the presented examples. The scope of the present invention is to be interpreted in the light of the accompanying claim set. In the context of the claims, the terms "including" or "includes" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An inhaler add-on device, the inhaler add-on device comprising:
    a housing comprising an air inlet, and an air outlet, wherein the housing defines a flow path between the air inlet and the air outlet, wherein the housing is configured to connect to an inhaler, and a first passive acoustic element arranged in the flow path inside the housing and dimensioned such that air flow passing the first passive acoustic element will generate sound with pre-determined characteristics depending on flow speed of air passing the first passive acoustic element, so as to allow acoustic monitoring of air flow passing the first passive acoustic element external to the housing, wherein the first passive acoustic element comprises a static structure having one or more gaps arranged to be passed by an air flow, and wherein the one or more gaps are shaped and separated by a distance so as to generate sound depending on air flow speed with pre-determined characteristics comprising at least spectral components, wherein the first passive acoustic element is configured to generate sound in response to inhaled air flow through the mouth piece, wherein the housing has a mouth piece in one end, and a fitting part at the opposite end, wherein the fitting part is configured to connect to the inhaler;

and a second passive acoustic element configured to generate sound in response to exhaled air flow through the mouth piece.

2. The inhaler add-on device according to claim 1, wherein the first passive acoustic element is a non-vibrating structure configured to generate sound by movement of air passing the passive acoustic element.

3. The inhaler add-on device according to claim 1, wherein the one or more gaps are shaped and separated by a distance so as to generate sound depending on flow speed with pre-determined characteristics comprising at least one spectral peak.

4. The inhaler add-on device according to claim 1, wherein said one or more gaps are straight gaps which are perpendicular or substantially perpendicular to a direction of air flow passing the first passive acoustic element.

5. The inhaler add-on device according to claim 1, wherein the first passive acoustic element comprises teeth defining one or more gaps between them, wherein the one or more gaps are a passage through the structure with no material being present in the one or more gaps.

6. The inhaler add-on device according to claim 1, wherein the first passive acoustic element is positioned in the flow path downstream of an inhaler medicament compartment configured to provide an inhalable medicament.

7. The inhaler add-on device according to claim 1, wherein the first passive acoustic element is positioned in the flow path upstream of an inhaler medicament compartment configured to provide an inhalable medicament.

8. The inhaler add-on device according to claim 1, wherein said device is configured to receive exhaled air via the air inlet or the air outlet, so as to generate sound with pre-determined characteristics depending on flow speed of air passing the first passive acoustic element, so as to allow acoustic monitoring of air flow passing the first passive acoustic element external to the housing upon a user exhaling air into the air inlet or air outlet.

9. The inhaler add-on device according to claim 1, wherein the first passive acoustic element is formed as a monolithic part of the housing.

10. The inhaler add-on device according to claim 1, wherein the housing and the first passive acoustic element are formed as a monolithic element.

11. The inhaler add-on device according to claim 1, wherein the mouth piece is configured to contact the user's mouth during inhalation, and wherein the fitting part is configured to connect to the inhaler by attachment of the fitting part to an air outlet of the inhaler.

12. The inhaler add-on device according to claim 1, wherein the fitting part is configured to lock the position of the inhaler add-on device to the inhaler.

13. The inhaler add-on device according to claim 12, wherein the fitting part is shaped so as to receive an air outlet pipe of the inhaler and to allow locking of the position of the inhaler add-on device to the inhaler upon insertion of the outlet pipe of the inhaler into the fitting part of the inhaler add-on device.

14. The inhaler add-on device according to claim 1, wherein the mouth piece has a first outer cross-sectional area, and wherein the fitting part has a second outer cross-sectional area being larger than the first outer cross-sectional area of the mouth piece.

15. The inhaler add-on device according to claim 14, wherein the mouth piece has a circular or elliptical outer cross-sectional shape.

16. The inhaler add-on device according to claim 1, wherein the housing is shaped to provide a straight flow path between the mouth piece and the fitting part.

17. The inhaler add-on device according to claim 1, wherein the first passive acoustic element is arranged inside the mouth piece and with one opening connected to the opening of the mouthpiece and, wherein an opposite opening of the first passive acoustic element is connected to the flow path inside the housing.

18. The inhaler add-on device according claim 1, wherein the first passive acoustic element is arranged in the flow path so as to receive a limited part of an air flow through the mouth piece.

19. The inhaler add-on device according to claim 18, wherein the first passive acoustic element is arranged in an air flow path between an opening of the housing and air flow inside the housing and, wherein the opening of the housing is separate from the mouth piece and the fitting part.

20. The inhaler add-on device according to claim 18, wherein the first passive acoustic element is arranged in a flow path with a direction which is perpendicular to a flow path direction in the mouth piece.

21. The inhaler add-on device according to claim 1, comprising wherein the second passive acoustic element comprises one or more gaps shaped and separated by a distance so as to generate sound depending on air flow speed with pre-determined spectral component characteristics, wherein the second passive acoustic element is configured to provide spectral component characteristics different from the first passive acoustic element.

22. The inhaler add-on device according to claim 1, wherein the mouth piece is configured to receive exhaled air, so as to allow acoustic monitoring of exhaled air flow external to the add-on device upon a user exhaling air into the mouth piece.

23. The inhaler add-on device according to claim 1, comprising a first valve configured to block exhaled air flow from passing the first passive acoustic element, and a second valve configured to block inhaled air flow from passing the second passive acoustic element.

24. The inhaler add-on device according to claim 23, wherein the first passive acoustic element and second passive acoustic element and the first valve and second valve are in the mouth piece.

25. The inhaler add-on device according to claim 1, further comprising a microphone configured to capture sound from the first passive acoustic element, and further configured to transmit data in response to captured sound using a wired or wireless connection to an external device.

26. The inhaler add-on device according to claim 25, wherein the microphone, and a processor circuit connected thereto are configured to transmit said data, and a battery for powering the processor circuit, are housed in a second housing separate from the first housing, wherein the second housing is configured to attach to the inhaler.

27. The inhaler add-on device according to claim 1, wherein the first passive acoustic element is connected to the housing.

28. A computer program configured to control a manufacturing system or device comprising at least one computer having a data storage configured to generate an inhaler add-on device according to claim 1.

29. A system comprising:
an inhaler add-on device according to claim 1, and
a device configured to capture sound generated by the inhaler add-on device during an inhalation, wherein the device comprises a processor configured to process the captured sound according to a processing algorithm and to generate a measure of air flow through the air outlet of the inhaler in response to the processing algorithm.

30. A method for measuring inhaled flow in an inhaler add-on device according to claim 1, the method comprising:
capturing sound external to the housing generated by the inhaler add-on device during a user inhaling a medicament through the air outlet of the inhaler add-on device,
processing the captured sound according to a processing algorithm, and
generating a measure of inhaled air flow through the air outlet of the inhaler add-on device in response to the processing algorithm.

31. A computer executable program code arranged to cause a device to perform the method according to claim 30, when executed on a processor.

* * * * *

UNITED STATES PATENT AND TRADEMARK OFFICE
CERTIFICATE OF CORRECTION

PATENT NO. : 11,666,714 B2
APPLICATION NO. : 16/624826
DATED : June 6, 2023
INVENTOR(S) : Jukka Rantanen It is certified that error appears in the above-identified patent and that said Letters Patent is hereby corrected as shown below:

In the Specification

Column 13, Line 12, delete "10b." and insert -- 10b --.

Column 16, Line 6, delete "monolith" and insert -- monolith. --.

Column 16, Line 26, delete "INDH." and insert -- INHD. --.

Column 16, Line 47, after "the" delete "the".

In the Claims

Column 20, Line 30, Claim 18, delete "according claim" and insert -- according to claim --.

Column 20, Line 44, Claim 21, after "claim 1," delete "comprising".

Signed and Sealed this
Seventeenth Day of October, 2023

*Katherine Kelly Vidal*
Katherine Kelly Vidal
*Director of the United States Patent and Trademark Office*